United States Patent [19]

Farino et al.

[11] Patent Number: 5,266,691
[45] Date of Patent: Nov. 30, 1993

[54] PROCESSES FOR MAKING CEPHEMS FROM ALLENYLAZETIDINONE DERIVATIVES

[75] Inventors: Vittorio Farino, West Hartford; Joydeep Kant, Meriden, both of Conn.

[73] Assignee: Bristol-Myers Squibb Company, New York, N.Y.

[21] Appl. No.: 928,863

[22] Filed: Aug. 11, 1992

Related U.S. Application Data

[62] Division of Ser. No. 711,249, Jun. 6, 1991, Pat. No. 5,162,524.

[51] Int. Cl.$^5$ .................. C07D 501/36; A61K 31/545
[52] U.S. Cl. .................................... 540/230; 540/222; 540/227; 540/215; 540/228
[58] Field of Search ............... 540/225, 215, 222, 227, 540/226, 228, 230

[56] References Cited

U.S. PATENT DOCUMENTS

| | | | |
|---|---|---|---|
| 4,550,162 | 10/1985 | Woodward et al. | 544/16 |
| 4,810,788 | 3/1989 | Torii | 540/358 |
| 4,853,468 | 8/1989 | Torii et al. | 540/222 |
| 5,132,419 | 7/1992 | Lanz et al. | 540/215 |

FOREIGN PATENT DOCUMENTS

507124A2 10/1992 European Pat. Off. .

OTHER PUBLICATIONS

Farina et al., Tetrahedron Letters, "Palladium Catalysis in Cephelosporin Chemistry," 29, No. 47, p. 6043 (1988).
Kant et al., Tetrahedron Letters, "Reactions of Organocuprates with Vinyl-triflates and Related Cephems," 31, No. 24, p. 3389 (1990).
Conway et al., Canadian Journal of Chemistry. "Nuclear Analogs of βLactam Antibiotics," 56, p. 1335 (1978).
Fleming et al., Tetrahedron, "The Silyl-cupration and Stannyl-cupration of Allenes," 45, No. 2, p. 413 (1989).
Corey et al., Tetrahedron Letters, "Synthesis of a New Series of Potent Inhibitors of Thromboxane $A_2$ Biosynthesis," 24, No. 32, p. 3291 (1983).
Ohmori et al., Tetrahedron Letters, "Stereocontrolled Synthesis of Steroid Side Chain," 23, No. 45, p. 4709 (1982).
Clinet et al., Nouveal Journal de Chemie, "An Efficient Method for the Preparation of Conjugated Allenic Carbonyl Compounds," 1, p. 373 (1977).

Primary Examiner—Nicholas S. Rizzo
Attorney, Agent, or Firm—William T. Han

[57] ABSTRACT

This invention relates to a novel process for making a cephem of formula II from a 2-(3-amino-2-oxo-azetidin-1-yl)-2,3-butadienoate intermediate of formula I using an organo-copper reagent. In another aspect, this invention is concerned with said intermediate.

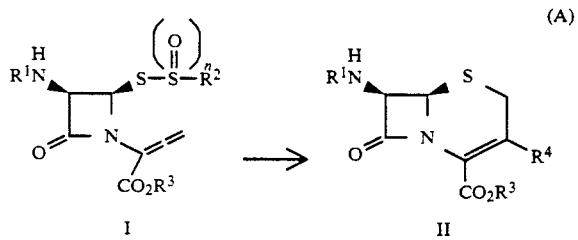

In the compounds of Scheme (A), $R^1$ is a conventional amino protecting group or an acyl group; $R^2$ is an aromatic heterocyclic or aryl group; $R^3$ is a conventional carboxy protecting group or $-CO_2R^3$ taken together forms a physiologically hydrolyzable ester; and $R^4$ is a group selected from the group consisting of $C_{1-6}$ alkyl, $C_{2-6}$ alkenyl, $C_{2-6}$ alkynyl, cyclic $C_{3-6}$ alkyl, and aryl; and n is 0 or 2.

21 Claims, No Drawings

PROCESSES FOR MAKING CEPHEMS FROM ALLENYLAZETIDINONE DERIVATIVES

CROSS REFERENCE TO RELATED APPLICATION

This application is a divisional application of pending Ser. No. 07/711,249, filed on Jun. 6, 1991, now U.S. Pat. No. 5,162,524.

BACKGROUND OF THE INVENTION

1. Field of Invention

This invention relates to a novel process for making antibacterial cephalosporins from allenylazetidinone derivatives.

More specifically, as shown in Scheme (A), the process involves converting 2-(3-amino-2-oxo-azetidin-1-yl)-2,3-butadienoate [allenylazetidinone] of formula I to a cephalosporin of formula II using an organo-copper reagent.

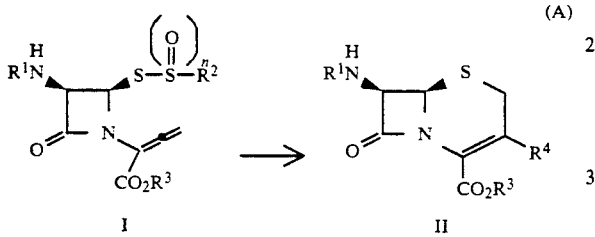

In Scheme (A), $R^1$, $R^2$, $R^3$, $R^4$, and n are defined hereinbelow.

2. Description of Related Art

Farina et al, in *Tetrahedron Letters*, 29, No. 47, p. 6043 (1988), disclose reactions of C-3 trifloxy cephalosporins of formula III with organo-stannanes in the presence of a palladium (0) catalyst to transfer a variety of $R^5$ radicals. Examples of $R^5$ radicals include alkenyl, alkynyl and aryl.

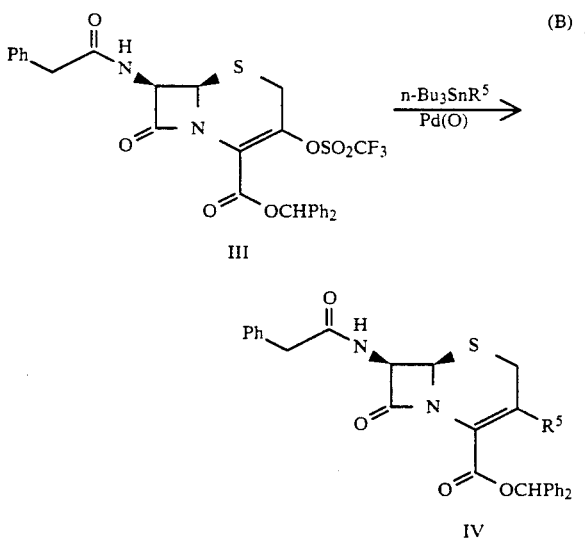

Similarly, Kant et al., in *Tetrahedron Letters*, 31, No. 24, p. 3389 (1990), disclose a process (Scheme C) whereby a compound of formula V is reacted with an organo-copper reagent $LiCu(R^6)$ or $Li_2Cu(CN)(R^6)_2$ to afford a compound of formula VI.

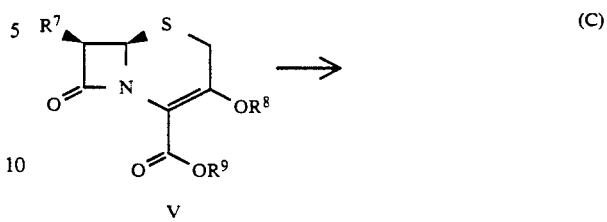

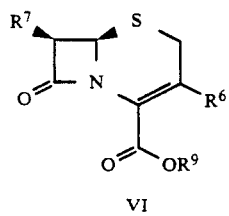

in Scheme (C), $R^6$ is alkyl, phenyl, or alkenyl; $R^7$ is $NHCOCH_2OPh$ or $NHCOCH_2Ph$; $R^8$ is $SO_2CF_3$, $SO_2C_6H_4$-p-$NO_2$, or $SO_2C_6H_4$-p-$CH_3$; and $R^9$ is $CHPh_2$ or $CH_2C_6H_4$-p-$OCH_3$.

Conway et al., in the *Canadian Journal of Chemistry*, 56, p 1335 (1978), disclose the allenylazetidinone derivative of formula VII.

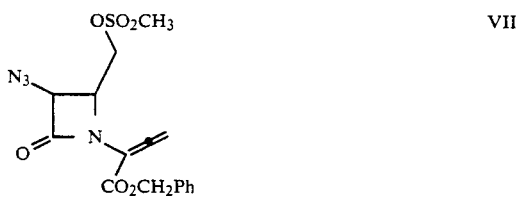

Due to the direct attachment of a methylene group to the C-4 position of the azetidinone ring, the compound of formula VII cannot be directly converted to a cephem structure.

U.S. Pat. No. 4,550,162, issued to Woodward et al on Oct. 29, 1985, discloses cephalosporins of formula VIII in which $R^{13}$ is an acyl group; $R^{11}$ represents an optionally substituted aromatic heterocyclic radical with up to 15, preferably up to 9, carbon atoms and at least one ring nitrogen atom and optionally a further ring heteroatom, such as oxygen or sulfur, which radical is bonded to the thio group —S— by one of its ring carbon atoms, which is bonded to a ring nitrogen atom by a double bond, or $R^{11}$ is —$SO_2Q'$ in which $Q'$ is an optionally substituted aliphatic, cycloaliphatic, araliphatic or aromatic hydrocarbon with up to 18, preferably up to 10, carbon atoms; and $R^{10}$ has the meaning of —$SO_2Q'$ as defined above.

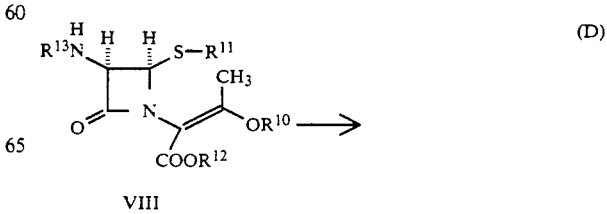

-continued

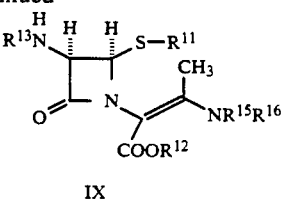

IX

The above compounds of formula VIII has never been converted to allenylazetidinones of the instant invention, but was transformed to the enamines of formula IX, in which $R^{11}$, $R^{12}$ and $R^{13}$ have the same meaning as above and $NR^{15}R^{16}$ is dialkylamino.

There has been several reports of reactions of allenylazetidinones with organo-copper reagents. Notably, for example, Fleming et al., in *Tetrahedron*, 45, No. 2, p. 413 (1989) disclose silyl cupration of the unsubstituted allene of formula X followed by direct treatment of the intermediate with an electrophile $E^+$, such as proton, carbon electrophile, or halogen to afford a compound of formula XI' or XI".

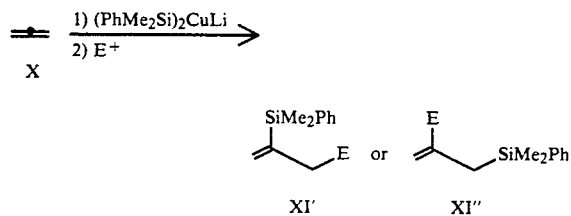

Other more remotely related examples of the reactions of organo-copper reagents with functionalized allenes can be found in: Corey et al., *Tetrahedron Letters*, 24, No. 32, p. 3291 (1983); Ohmori et al., *Tetrahedron Letters*, 23, No. 45, p. 4709 (1982); and Clinet et al., *Nouveal Journal de Chemie*, 1, p. 373 (1977).

SUMMARY OF THE INVENTION

As shown in Scheme (A), this invention relates to a novel process for making a cephem of formula II from a 2-(3-amino-2-oxo-azetidin-1-yl)-2,3-butadienoate intermediate of formula I using an organo-copper reagent. In another aspect, this invention is concerned with said intermediate.

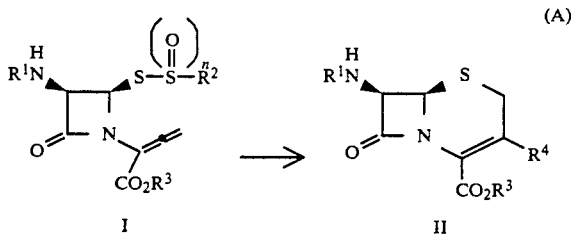

In the compounds of Scheme (A), $R^1$ is a conventional amino protecting group or an acyl group; $R^2$ is an aromatic heterocyclic or aryl group; $R^3$ is a conventional carboxy protecting group or $-CO_2R^3$ taken together forms a physiologically hydrolyzable ester; and $R^4$ is a group selected from the group consisting of $C_{1-6}$ alkyl, $C_{2-6}$ alkenyl, $C_{2-6}$ alkynyl, cyclic $C_{3-6}$ alkyl, and aryl; and n is 0 or 2.

DETAILED DESCRIPTION OF THE INVENTION

This invention relates to a novel process, as shown in Scheme (A), for making a cephem of formula II from a 2-(3-amino-2-oxo-azetidin-1-yl)-2,3-butadienoate (allenylazetidinone) intermediate of formula I. The reagent used in effecting the process is an organo-copper reagent. In another aspect, this invention is concerned with said allenylazetidinone intermediate.

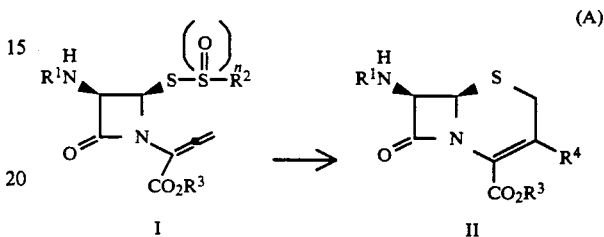

In the compounds of Scheme (A), $R^1$ is a conventional amino protecting group or an acyl group; $R^2$ is an aromatic heterocyclic or aryl group; $R^3$ is a conventional carboxy protecting group or $-CO_2R^3$ taken together forms a physiologically hydrolyzable ester; and $R^4$ is a group selected from the group consisting of $C_{1-6}$ alkyl, $C_{2-6}$ alkenyl, $C_{2-6}$ alkynyl, cyclic $C_{3-6}$ alkyl, and aryl; and n is 0 or 2.

More specifically, in compounds of Scheme (A), when $R^1$ is an acyl group as distinguished from a conventional amino protecting group, said acyl group is selected from the pharmacologically active C-7 or C-6 acyl side chains found in the respective cephalosporin or penicillin antibiotic art. Preferable acyl group is that from the cephalosporin art. A recent review by Durckheimer et al., "Recent Developments in the Field of Cephem Antibiotics", *Advances in Drug Research*, 17, pp 61-234 (1988), offers a comprehensive overview of cephalosporin antibiotic art and possible C-7 acyl side chains.

When the acyl group $R^1$ is represented by a radical $R^8CO-$, preferred $R^a$ is hydrogen;

$C_{1-6}$ alkyl, $C_{1-6}$ alkyl substituted by cyano, carboxy, halogen, amino, $C_{1-6}$ alkyloxy, $C_{1-6}$ alkylthio, trifluoromethyl, or trifluoromethylthio;

a phenyl or substituted phenyl group represented by the formula

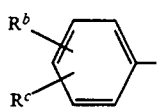

wherein $R^b$ and $R^c$ independently are hydrogen, halogen, hydroxy, $C_{1-6}$ alkyloxy, $C_{1-6}$ alkyl, $C_{1-6}$ alkylthio, amino, mono- or di($C_{1-6}$ alkyl)amino, $C_{1-6}$ alkanoylamino, $C_{1-6}$ alkylsulfonylamino, carboxy, carbamoyl, hydroxymethyl, aminomethyl, or carboxymethyl;

a group presented by the formula

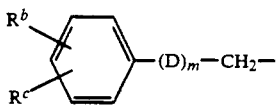

wherein $R^b$ and $R^c$ have the same meanings as defined above, D is oxygen or sulfur, and m is 0 or 1;

a heteroarylmethyl group represented by the formula

wherein $R^d$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_{1-6}$ alkyl, $C_{1-6}$ alkyloxy, $C_{1-6}$ alkysulfonylamino;

a substituted methyl group represented by the formula

wherein $R^e$ is cyclohexa-1,4-dienyl, or a phenyl group or substituted phenyl group

wherein $R^b$ and $R^c$ have the above defined meanings, or $R^e$ is $R^d$ as defined above, and Z is hydroxy, $C_{1-6}$ alkanoyloxy, carboxy, sulfo, or amino;

a keto group or an oximino-substituted group represented by the formulae

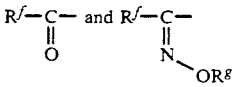

wherein $R^f$ is $R^d$ or $R^e$ as defined above and $R^g$ is hydrogen, $C_{1-6}$ alkyl, cyclic $C_{3-6}$ alkyl or a radical selected from the formulae

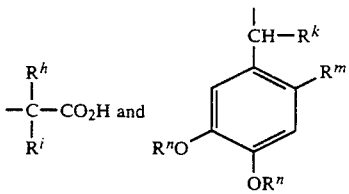

in which $R^h$ and $R^i$ are independently hydrogen, methyl or ethyl, or $R^h$ and $R^i$, taken together with the carbon atom to which they are attached, may be a cycloalkylidene ring containing from 3 to 5 carbon atoms, $R^k$ and $R^m$ are hydrogen or carboxy, with the proviso that both cannot be the same, and $R^n$ is hydrogen or acetyl; or an alkylidene group of the formulae

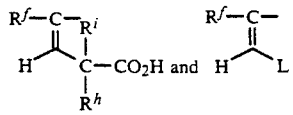

in which L is halogen or $CF_3$, and $R^f$, $R^i$ and $R^h$ are as defined above.

More preferred $R^a$ group is a radical selected from the group

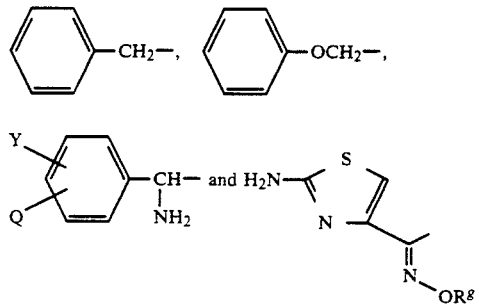

in which Y and Q are independently hydrogen, hydroxy or halogen; $R^g$ is hydrogen, $C_{1-6}$ alkyl, cyclic $C_{3-6}$ alkyl or a radical of the formula

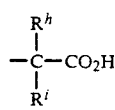

in which $R^h$ and $R^i$ are as defined above.

In the instant application, the numbers in subscript after the symbol "C" define the number of carbon atoms a particular group could contain. For example, in the above definition of the compounds in Scheme (A), $C_{1-6}$ alkyl refers to straight and branched chain alkyl groups with one to six carbon atoms and such groups include methyl, ethyl, n-propyl, isopropyl, n-butyl, t-butyl, n-pentyl, n-hexyl, 3-methylpentyl and the like alkyl groups. Similarily, $C_{1-6}$ alkyloxy (alkoxy) refers straight or branched alkyloxy groups such as methoxy, ethoxy, n-propoxy, i-propoxy, n-butoxy, t-butoxy, n-pentyloxy, n-hexyloxy, 3-methylpentyloxy, to name a few; $C_{2-6}$ alkenyl refers to straight or branched alkenyl groups such as vinyl, allyl, 1-propenyl, isopropenyl, 1-butenyl, 2-butenyl, 3-butenyl, methallyl, 1,1-dimethylallyl, 1-hexenyl, 2-hexenyl and the like groups; $C_{2-6}$ alkynyl refers to straight or branched chain alkynyl groups such as ethynyl, 1-propynyl, propargyl, 1-hexynyl, 2-hexynyl and the like groups; $C_{1-6}$ akanoyloxy refers to groups such as formyloxy, acetoxy (acetyloxy), propanoyloxy, 3-methylpentanoyloxy and the like groups; cyclic $C_{3-6}$ alkyl refers to groups such as cyclopropyl, cyclobutyl, cyclopentyl, cyclohexyl, cyclopropylmethyl, cyclopropylethyl, cyclopropylpropyl, cyclobutylmethyl, cyclobutylethyl, cyclopentylmethyl and the like groups; aryl group refers to unsubstituted phenyl or phenyl independently substituted with one to three halogen, $C_{1-6}$ alkyl, $C_{1-6}$ alkyloxy or $C_{1-6}$ alkylthio such as 4-methylphenyl (p-toluene), 2,3-dimethoxyphenyl, 2-methyl-3-ethoxyphenyl, 4-t-butoxyphenyl, 4-methylthio-3-fluorophenyl, 2,4-dichlorophenyl, 2-chloro-4-bromophenyl and the like groups; di($C_{1-6}$ alkyl)amino refers to disubstituted amino groups in which the two substituents may be the same or different, such as dimethylamino, N-ethyl-N-methylamino, N-ethyl-N-propylamino, diethylamino and the like groups; $C_{1-6}$ alkyl substituted by cyano refers to cyanomethyl, cyanoethyl, 4-cyanobutyl and the like; $C_{1-6}$ alkyl substituted by carboxy refers to such groups as carboxymethyl, 2-carboxyethyl, 2-carboxypropyl, 4-carboxybutyl, 5-carboxypentyl and the like; halogen refers to fluorine, chlorine, bromine, or iodine; thus, $C_{1-6}$ alkyl substituted by halogen refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl and the like; $C_{1-6}$ alkyl substituted by amino refers to such groups as 2-aminoethyl, aminomethyl, 3-aminopropyl, and 4-aminobutyl and the like groups; $C_{1-6}$ alkyl substituted by $C_{1-6}$ alkyloxy (alkoxy) refers to methoxymethyl, 2-methoxyethyl, 2-ethoxyethyl, ethoxymethyl, 3-propoxypropyl, 3-ethoxybutyl, 4-t-butoxybutyl, 3-methoxypentyl, 6-methoxyhexyl, 5-pentyloxyhexyl and the like groups; $C_{1-6}$ alkyl substituted by $C_{1-6}$ alkythio refers to such groups as methylthiomethyl, 2-methylthioethyl, 2-ethylthiopropyl, 4-methylthiobutyl, 5-ethylthiohexyl, 3-t-butylthiopropyl, 3-hexylthiopropyl and the like groups; $C_{1-6}$ alkyl substituted by trifluoromethyl is exemplified by 2,2,2-trifluoroethyl, 3,3,3-trifluoropropyl, 4,4,4-trifluorobutyl and the like; and $C_{1-6}$ alkyl substituted by trifluoromethylthio refers to, for example, trifluoromethylthiomethyl, 2-trifluoromethylthioethyl, 2-trifluoromethylthiopropyl, 4-trifluoromethylthiobutyl, 5-trifluoromethylthiohexyl and the like $C_{1-6}$ alkyl substituted groups.

When $R^a$ is a substituted phenyl group wherein the substituents are represented by $R^b$ and $R^c$, examples of such groups are halophenyl such as 4-chlorophenyl, 3-bromophenyl, 2-fluorophenyl, 2,4-dichlorophenyl and 3,5-dichlorophenyl; hydroxyphenyl such as 2-hydroxyphenyl, 3-hydroxyphenyl, 4-hydroxyphenyl, 2,4-dihydroxyphenyl and 3,4-dihydroxyphenyl; alkyloxyphenyl such as 2,6-dimethoxyphenyl, 4-methoxyphenyl, 3-ethoxyphenyl, 3,4-dimethoxyphenyl, 4-t-butoxyphenyl, 4-methoxy-3-ethoxyphenyl and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl and 3,5-dimethylphenyl; alkylthiophenyl such as 4-methylthiophenyl, 3-n-butylthiphenyl, 2-ethylthiphenyl, 3,4-dimethylthiophenyl and 3-n-propylthiophenyl; aminophenyl such as 2-aminophenyl, 4-aminophenyl, 3,5-diaminophenyl and 3-aminophenyl; alkanoylaminophenyl such as 2-acetylaminophenyl, 4-acetylaminophenyl, 3-propionylaminophenyl and 4-butyrylaminophenyl; alkylsulfonylaminophenyl such a 3-methylsulfonylaminophenyl, 4-methylsulfonylaminophenyl, 3,5-(dimethylsulfonylamino)phenyl, 4-n-butylsulfonylaminophenyl and 3-ethylsulfonylaminophenyl; carboxyphenyl such as 2-,3-, or 4-carboxyphenyl, 3,4-dicarboxyphenyl and 2,4-dicarboxyphenyl; carbamoylphenyl such as 2-carbamoylphenyl, 2,4-dicarbamoylphenyl and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxymethylphenyl such as 2-carboxymethylphenyl, 4-carboxymethylphenyl and 3,4-dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butoxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-methoxy-3-hydroxyphenyl, 4-methylsulfonylamino-2-carboxyphenyl, 4-amino-3-chlorophenyl and 2-carboxymethyl-4-hydroxyphenyl.

Examples of $R^aCO$-groups wherein $R^a$ is a group represented by the formula

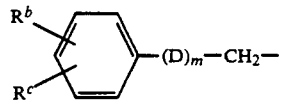

with m equals 0 are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl and 4-acetylaminophenylacetyl; and with m equals 1 and D equals oxygen, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m equals 1 and D equals sulfur, phenylthioacetyl, 4-chlorophenylthioacetyl, 3,4-dichlorophenylthioacetyl, 2-fluorophenylthioacetyl, 3-hydroxyphenylthioacetyl and 4-ethoxyphenylthioacetyl.

Examples of $R^d$—$CH_2CO$ groups wherein $R^d$ is a heteroaryl group are 2-thienylacetyl, 3-thienylacetyl, 2-furylacetyl, 2-benzothienylacetyl, 2-benzofurylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl and the like heteroaryl groups optionally substituted by amino, $C_{1-6}$ alkylsulfonylamino, hydroxy, halogen, $C_{1-6}$ alkyl or $C_{1-6}$ alkyloxy groups.

Examples of $R^1CO$ -groups wherein $R^a$ is a substituted methyl group represented by the formula $R^e$—CH(Z)— and Z is amino, carboxy, hydroxy, $C_{1-6}$ alkanoyloxy, or sulfo are 2-carboxy-2-phenylacetyl, 2-carboxy-2-(4-hydroxyphenyl)acetyl, 2-amino-2phenylacetyl, 2-amino-2-(4-hydroxyphenyl)acetyl, 2-amino-2-(3-chloro-4-hydroxyphenyl)acetyl, 2-amino-2-(cyclohexa-1,4-dien-1-yl)acetyl, 2-hydroxy-2-phenylacetyl, 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2yl)acetyl.

Examples of $R^aCO$ acyl groups in which $R^a$ is a keto group or an oximino-substituted group represented by the formulae

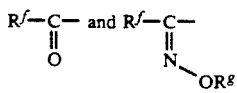

are the keto groups such as 2-oxo-2-phenylacetyl, 2-oxo-2-(2-thienyl)acetyl and 2-oxo-2-(2-aminothiazol-4-yl)acetyl; and the oximino-substituted groups such as 2-phenyl-2-methoxyiminoacetyl, 2-(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)iminoacetyl, 2-(5-amino-1,2,4-thiadiazol-3-yl)-2-methoxyiminoacetyl, 2-(2-aminothiazol-4-yl)-2-methoxyiminoacetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-(2-carbamoyl-prop-2-yl)oxyiminoacetyl and 2-(5-amino-1,3,4-thiadiazol-2-yl)-2-methoxyiminoacetyl.

Examples of $R^aCO$ acyl groups wherein $R^a$ is an alkylidene represented by the formulae

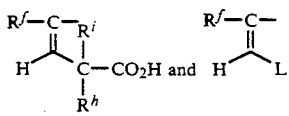

are 2-(2-aminothiazol-4-yl)-2-(2,2-dimethyl-2-carboxyethylidene)acetyl, 2-(2-aminothiazol-4-yl)-2-(2-trifluoroethylidene)acetyl and the like.

As used in the instant invention, an aromatic heterocylic group $R^2$, as opposed to a heteroaryl group $R^d$ defined previously, refers to a five-membered aromatic heterocyclic ring containing 1 to 4 nitrogen atoms, and up to 1 sulfur or 1 oxygen atom, said five-membered ring optionally substituted with up to four $C_{1-6}$ alkyl groups or a benzo group; or said aromatic heterocylic group also refers to a six-membered aromatic heterocylic ring containing 1 to 4 nitrogen atoms and optionally substituted with up to four $C_{1-6}$ alkyl groups. Said aromatic heterocylic group is connected to the C-3 sulfur atom of the cephalosporins through an unsubstituted carbon atom in the ring. Preferred aromatic heterocylic groups include groups such as benzothiazol-2-yl, benzoxazol-2-yl, 1-methylbenzimidazol-2-yl, 2-pyridyl, oxazol-2-yl, thiazol-2-yl, 1-methyl-1,2,3,4-tetrazol-5-yl and 1-methylimidazol-2-yl.

Conventional carboxy-protecting groups which can be employed in the present invention to block or protect the carboxylic acid function are well-known to those skilled in the art and, preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation. Examples of such readily removable carboxy-protecting groups include moieties such as $C_{1-6}$ alkyl, diphenylmethyl (benzyhydryl), 2-naphthylmethyl, 4-pyridylmethyl, phenacyl, acetonyl, 2,2,2-trichloroethyl, silyl such as trimethylsilyl and t-butyldimethylsilyl, phenyl, ring substituted phenyl, e.g., 4-chlorophenyl, tolyl, and t-butylphenyl, phenyl $C_{1-6}$ alkyl, ring substituted phenyl $C_{1-6}$ alkyl, e.g., benzyl, 4-methoxybenzyl, 4-nitrobenzyl (p-nitrobenzyl), 2-nitrobenzyl (o-nitrobenzyl), and triphenylmethyl (trityl), methoxymethyl, 2,2,2-trichloroethoxycarbonyl, benzyloxymethyl, $C_{1-6}$ alkanoyloxy $C_{1-6}$ alkyl such as acetoxymethyl, propionyloxymethyl, $C_{2-6}$ alkenyl such as vinyl and allyl. Other suitable carboxy protecting groups well known in the art which have not been disclosed above can be found in "Protective Groups in Organic Synthesis", Theodora W. Greene (John Wiley & Sons, 1981), Chapter 5 incorporated herein by reference. Particularly advantageous carboxy protecting groups are benzyl, p-nitrobenzyl, o-nitrobenzyl, 2,4-dimethoxybenzyl, 4-methoxybenzyl, allyl, substituted allyl, t-butyl or diphenylmethyl (DPM).

Conventional amino protecting groups are also well-known to those skilled in the art and have reference to groups commonly employed in protecting or blocking the amino functional group during a reaction step and which can be split off subsequently without destroying or substantially altering the remaining portion of the molecule. Examples include vinyl, allyl, t-butoxycarbonyl, benzyl, benzyloxycarbonyl, 2-nitrobenzyl, 4-nitrobenzyl, 2-nitrobenzyloxylcarbonyl, formyl, benzoyl, acetyl, ethylcarbonyl, chloroacetyl, trichloroacetyl, trifluoroacetyl, methoxycarbonyl, allyloxycarbonyl, trimethylsilyl, triethylsilyl, triphenylsilyl, t-butyl-dimethylsilyl, methyldiphenylsilyl, 2,4-dimethoxybenzyl, 2,4-dimethoxybenzyloxycarbonyl, 4-methoxybenzyl, 4-(methoxymethoxy)phenyl, bis-(4-methoxyphenyl)-methyl, t-butoxycarbonylmethyl, allyoxycarbonylmethyl, methoxymethyl, methylthiomethyl, methoxyethoxymethyl, 2-(trimethylsilyl)ethoxy]methyl or 2-(methylthiomethoxy)ethoxycarbonyl. In general, amino protecting groups which are readily removed under acid conditions or catalytic hydrogenolysis are preferred, e.g. t-butoxycarbonyl, benzyloxycarbonyl and triphenylmethyl. Other suitable amino protecting groups well known to those skilled in the art can be found in "Protective Groups in Organic Synthesis", Theodora W. Greene (John Wiley & Sons, 1981), Chapter 7, incorporated herein by reference.

The physiologically hydrolyzable esters serve as prodrugs by being hydrolyzed in the body to yield the antibiotic per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkyl, benzyl, 4-methoxybenzyl, indanyl, phthalidyl, methoxymethyl, $C_{1-6}$ alkanoyloxy $C_{1-6}$ alkyl, e.g. acetoxymethyl, pivaloyloxymethyl or propionyloxymethyl, $C_{1-6}$ alkoxycarbonyloxy $C_{1-6}$ alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other physiologically hydrolyzable esters known and used in the penicillin and cephalosporin arts. Such esters are prepared by conventional techniques known in the art.

The structural formulae as drawn herein are believed to best represent the structures of compounds of the present invention. However, some compounds within the scope of the invention may exist as other tautomeric forms, in which hydrogen atoms are transposed to other parts of the molecules and the chemical bonds between the atoms of the molecules are consequently rearranged. It should be understood that the structural formulae represent all tautomeric forms, insofar as they may exist.

The above mentioned compounds also could have several asymmetric carbon atoms and thus could exit in several stereochemical forms. The instant processes are intended to be applicable to a mixture of isomers and to a single stereoisomer. However, in the instant allenylazetidinones, the 3R and 4R configurations are preferred on the azetidinone rings. Further, the 6R and 7R configurations are preferred on cephems of formula II. Moreover, when $R^a$ is of the radical

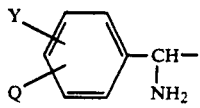

the "D" configuration at the benzylic carbon is preferred.

Besides the tautomeric and asymmetric stereoisomerisms which may exist in the compounds of the present application, there can be "syn" (Z) and "anti" (E) stereoisomerism arising from different orientations of substituent(s) on a double bond. Unless otherwise explicitly stated, the present processes can be applied to a pure isomer and to a mixture of "syn" and "anti" isomers. For example, when a compound of formula I or II has an oximino radical substituted with an aminothiazolyl or aminothiadiazolyl ring represented by the formula

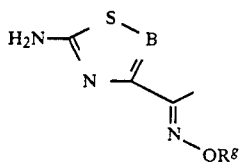

as $R^a$, and in which B and $R^g$ are as previously defined, the imino group has either the "syn" (Z) or "anti" (E) configuration. The radical is drawn as the "syn" isomer. The processes which involve the oximino radicals with at least 90% of the "syn" isomers are preferred. Preferably the above-mentioned radicals are the "syn" isomers which is essentially free of the corresponding "anti" isomers.

DESCRIPTION OF SPECIFIC EMBODIMENT

A compound of formula I in Scheme (A) can be made by a process depicted in Scheme (E).

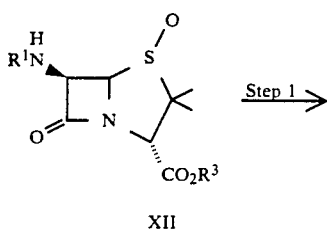

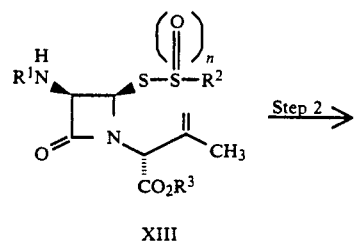

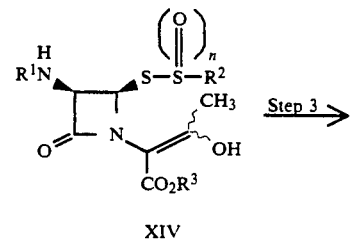

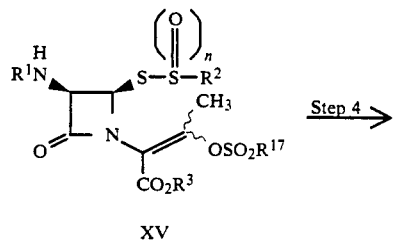

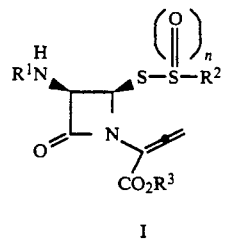

In scheme (E), $R^1$, $R^2$, $R^3$ and n are defined previously. A penam sulfoxide of formula XII are either known or can be made from known processes well established in the art. The conversion of a penam sulfoxide XII to a dithioazetidinone enol of formula XIV can be effected by various processes as disclosed, for example, in *Tetrahedron Letters*, No. 32, pp 3001-3004 (1973), U.S. Pat. Nos. 4,255,328, 4,550,162, or 4,798,890 or in the references cited therein.

The general process to transform an enol of formula XIV into a sulfonic ester formula XV is well described in U.S. Pat. No. 4,550,162. More specifically, compounds of formula XIV is esterified with a reactive functional derivative of a sulphonic acid of the formula HO—$SO_2$—$R^{17}$, wherein $R^{17}$ is $C_{1-6}$ alkyl optionally substituted with up to 13, preferably up to 3, halogen atoms, halogen, aryl, or —$NO_2$ substituted phenyl. Most preferably, $R^{17}$ is a group selected from $CH_3$, $CF_3$, 4-nitrophenyl and 4-methylphenyl. The applicants have discovered that $R^{17}$ can also be F, which is further subject of the present invention.

The reactive functional derivatives of a sulphonic acid of the formula HO—$SO_2$—$R^{17}$ which are used are, for example, their reactive anhydrides, especially the mixed anhydrides with hydrogen halide acids, for example their chloride, such as mesyl chloride and p-toluenesulphonic acid chloride. Straight anhydrides can also be used such as fluorosulfonic anhydride. The esterification is carried out, preferably in the presence of an organic tertiary nitrogen base, such as pyridine, triethylamine, N,N-diisopropyl-N-ethylamine (diisopropylethylamine), in a suitable inert solvent, such as aliphatic, cycloaliphatic or aromatic hydrocarbon, such as hexane, cyclohexane, benzene or toluene, a halogenated aliphatic hydrocarbon, for example methylene chloride, or an ether, such as a di-($C_{1-6}$) alkyl ether, for example diethyl ether, or a cyclic ether, for example tetrahydrofuran or dioxane, or in a solvent mixture.

The elimination of the sulfonyl leaving group in Step 4 is achieved with a base. Examples of suitable bases for the elimination are organic nitrogen-containing bases, such as tertiary heterocyclic bases of aromatic character, and above all tertiary aliphatic, azacycloaliphatic or aralphatic bases: such as N,N,N-tri-$C_{1-7}$ alkylamines, for example, N,N,N-trimethylamine, N,N-dimethyl-N-ethylamine, N,N,N-triethlamine or N,N-diisopropyl-N-ethylamine; N-$C_{1-7}$ alkyl-azacycloalkanes, for example N-methylpiperidine or N-phenyl-$C_{1-7}$ alkyl-N,N-di-$C_{1-7}$ alkylamines, for example, N-benzyl-N,N-dimethylamine, as well as mixture thereof, such as the mixture of a base of the pyridine type, for example, pyridine and a N,N,N-tri-$C_{1-7}$ alkylamine, for example, pyridine and triethylamine.

The process in Scheme (A) above can be effected with a variety of organo-copper reagents. The preferred organo-copper reagents can be classified into the following three categories:

1) Simple organo-copper reagents represented by the empirical formula $R^4$-Cu;
2) Lower order organo cuprates represented by the empirical formula $R^4R'$CuM or $R^4$LCuM; and
3) Higher order organo cuprates represented by the empirical formula $R^4R'R''$CuM$_2$, $R^4R'$LCuM$_2$ or $R^4$L'L''CuM$_2$.

In the above formulas for the organo-copper reagents, $R^4$, $R'$ and $R''$ are independently $C_{1-6}$ alkyl, $C_{2-6}$ alkenyl, $C_{3-6}$ cyclic alkyl, aryl, or $C_{2-6}$ alkynl. Preferably, $R^4$, $R'$ and $R''$ represent the same group in an organo-copper reagent; when they all do not represent the same group, the organo-copper reagent is referred to as a mixed organo-copper reagent. L and L' independently represent non-transferable ligands; examples include such as, but not limited to, Br$^-$, Cl$^-$, CN$^-$, 2-thienyl or SCN$^-$. M represents a cation, typically, such as Li$^+$, $^+$N(n-Bu)$_4$, $^+$Mg Cl, $^+$MgBr, or $^+$MgI.

The above organo-copper reagents can be optionally bound to a neutral coordinating ligand. For example, typical coordinating ligands for the simple organo-copper reagents are Me$_2$S, BF$_3$, P(OCH$_3$)$_3$, P($C_{1-10}$ alkyl)$_3$ or MgXX' in which X and X' are independently Cl$^-$, Br$^-$ or I$^-$. For the lower organo cuprates, examples of neutral ligands include, but are not limited to, P($C_{1-10}$ alkyl)$_3$, P(OCH$_3$)$_3$, LiI or O=P[N(CH$_3$)$_2$]$_2$.

The process in Scheme (A) is preferably effected between the temperature of 0° C. to −100° C., more preferably between −78° C. to −100° C.

The desirable solvent used in the step in Scheme (A) is aprotic. Thus, for example, the solvent may be selected from 1-methyl-2-pyrrolidinone, tetrahydrofuran (THF), hexane, pentane, 1,2-dimethoxyethane (DME), benzene, toluene, xylene, dimethylsulfoxide (DMSO), dimethylformamide (DMF), dioxane, glyme, hexamethylphosporic amide (HMPA), etc. Furthermore, the solvent may be a mixed solvent. Most preferably, the solvent is THF.

The preparation of organo-copper reagents has been well described in literature. Among many publications which can be relied to make the above described organo-copper reagents include (a) Posner, G. H., *An Introduction to Synthesis Usinq Organocopper Reagents*, Wiley, N.Y. (1980); (b) Posner, G. H., *Organic Reactions*, 19, p. 1 (1972); (c) Posner, G. H., *Organic Reactions*, 22, p. 253 (1975); and (d) Lipshultz, B. H., *Synthesis*, p. 325 (1987).

Needless to say that in carrying out the steps described in either Scheme (A) or (E), when $R^1$ is an acyl group as defined previously and if such acyl group contains one or more free amino, hydroxy and/or carboxy groups, such groups may be protected with conventional amino, hydroxy and/or carboxy protecting groups. Similarly when COOR$^3$ is a physiologically hydrolyzable ester and if such physiologically hydrolyzable ester contains one or more free amino, hydroxy and/or carboxy groups, such groups may also be protected with conventional amino, hydroxy and/or carboxy protecting groups.

As used herein, conventional hydroxy protecting groups which can be employed in the present invention to block or protect the hydroxy function are well-known to those skilled in the art and, preferably, said groups can be removed, if desired, by methods which do not result in any appreciable destruction of the remaining portion of the molecule, for example by chemical or enzymatic hydrolysis. Examples of such readily removable hydroxy protecting groups include methoxymethyl, 2,2,2-trichloroethyoxymethyl, tetrahydropyranyl, tetrahydrofuranyl, t-butyl, benzyl, p-methoxybenzyl, diphenylmethyl, trialkylsilyl, triphenylsilyl, and the like. Other suitable protecting groups are disclosed in "Protecting Groups in Organic Synthesis", Theodora W. Greene (John Wiley & Sons, 1981), Chapter 2 for hydroxy, which is hereby incorporated by reference.

The specific examples which follow illustrate the synthesis of representative compounds of the instant invention and are not construed as limiting the invention in sphere or scope. The methods may be adopted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (br s), broad doublet (br d), broad triplet (br t), broad quartet (br q), singlet (s), multiplet (m), doublet (d), quartet (q), triplet (t), doublet of doublet (dd), doublet of triplet (dt), and doublet of quartet (dq). The solvents employed for taking NMR spectra are DMSO-d$_6$ (perdeuterodimethysulfoxide), D$_2$O (deuterated water), CDCl$_3$ (deuterochloroform) and other conventional deuterated solvents. The infrared (IR) spectral description include only absorption wave numbers (cm$^{-1}$) having functional group identification value. When used in reference to an infrared spectrum, s refers to sharp and vs refers to very sharp.

Celite is a registered trademark of the Johns-Manville Products Corporation for diatomaceous earth.

Except otherwise indicated, ether normally refers to diethyl ether.

The abbreviations used herein are conventional abbreviations widely employed in the art. Some of which are:

| | |
|---|---|
| FAB: | Fast Atom Bombardment |
| DMSO: | dimethyl sulfoxide |
| Boc: | t-butoxycarbonyl |
| DPM: | diphenylmethyl |
| Ph: | phenyl |
| tBu: | t-butyl |
| HPLC: | High pressure liquid chromatography |
| PNB: | 4-nitrobenzyl |
| Tf: | trifluoromethanesulfonyl |

EXAMPLE 1

Diphenylmethyl 2-[(3R, 4R)-4-[(benzothiazol-2-yl)dithio]-3-phenoxyacetamido-2-oxo-azetidin-1-yl]-3-methyl-3-butenoate (XIIIa)

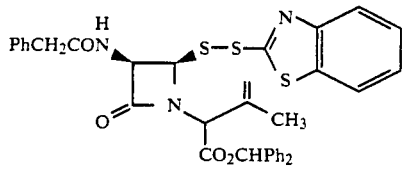

To a solution of diphenylmethyl penicillin V oxide (11.53 g, 0.0223 mole) in toluene (120 mL), 2-mercaptobenzothiazole (3.8 g, 0.0227 mole) was added and the mixture refluxed through a Dean-Stark trap. After 2.5 h, no starting material was detected by thin-layer chromatography. The solution was cooled, filtered through charcoal and Celite, concentrated to a volume of 30–40 mL and cooled to 0° C. Ether (40–50 mL) was added slowly; the crystalline precipitate was filtered and washed with a small portion of cold ether, and then dried in vacuo to afford 12.43 g (83.7%) of the title compound.

ANALYTICAL DATA $^1$H-NMR (CDCl$_3$, 360 MHz) δ7.8 (d, 1H), 7.6 (d, 1H), 7.5–7.1 (m, 15H), 6.98 (t, 1H), 6.94 (d overlapping s, 3H overall), 5.6 (d, J=5.0 Hz, 1H), 5.42 (dd, J=5.0; 7 Hz, 1H), 5.1 (s, 1H), 5.05 (s, 1H), 4.9 (s, 1H), 4.5 (dd, 2H), 1.95 (s, 3H).

EXAMPLE 2

Diphenylmethyl 2-[(3R, 4R)-4-(p-toluenesulfonylthio)-3-phenoxyacetamido-2-oxo-azetidin-1-yl]-3-methyl-3-butenoate (XIIIb)

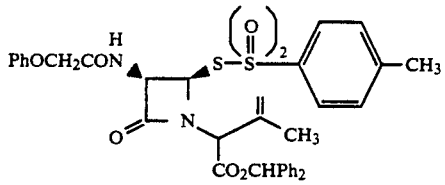

To a solution of diphenylmethyl 2-[(3R,4R)-4-[(benzothiazol-2-yl)dithio]-3-phenoxyacetamido-2-oxo-azetidin-1-yl]-3-methyl-3-butenoate (XIIIa. 12.12 g, 0.0182 mole) in acetone (325 mL) and water (37 mL), silver nitrate (3.86 g, 0.0227 mole) was added all at once. A freshly prepared solution of sodium p-toluenesulfinate hydrate (4.05 g; 0.0227 mole) in acetone (255 mL) and water (37 mL) was added dropwise over 1 h, while the reaction mixture was protected from light. After an additional 1h period at room temperature, Celite (5 g) was added and the mixture was diluted with acetone (500 mL) and then was filtered. The filtrate was evaporated to a small volume, and the crude product was extracted into ether (3×250 mL). The ether phase was dried with magnesium sulfate and concentrated to afford a crude product. Flash chromatography (SiO$_2$, eluting with 40% ethyl acetate in hexane) gave 9.05 g (73.5%) of the title compound as a white solid.

ANALYTICAL DATA $^1$H-NMR (CDCl$_3$ 360 MHz) δ7.62 (d, 2H), 7.35–7.00 (m, 15H), 6.85 (d, 2H), 5.90 (d, J=5 Hz, 1H), 5.22 (dd, J=5; 7 Hz, 1H), 4.90 (s, 1H), 4.79 (s, 1H), 4.41 (s overlapping dd, 3H overall), 2.32 (s, 3H), 1.80 (s, 3H).

EXAMPLE 3

4-Nitrobenzyl 2-[(3R,4R)-4-[(benzothiazol-2-yl)dithiol-3-phenoxyacetamido-2-oxo-azetidin-1-yl]-3-methyl-3-butenoate (XIIIc)

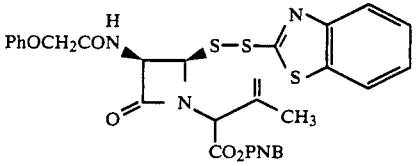

To a solution of 4-nitrobenzyl penicillin V oxide (4.73 g, 0.010 mole) in toluene (100 mL), 2-mercaptobenzothiazole (1.67 g, 0.010 mole) was added and the mixture refluxed through a Dean-Stark trap until no starting material was detected by thin-layer chromatography (4 h). The toluene solution was cooled, the volume was reduced until some precipitation occurred, and the crystallization was allowed to proceed at 0° C. overnight.

Yield: 4.98 g (80%) of the title compound, XIIIc, as off-white crystals.

ANALYTICAL DATA $^1$H-NMR (CDCl$_3$, 360 MHz) δ8.18 (d, 2H), 7.8 (d, 1H), 7.6 (d, 1H), 7.5–7.2 (m, 7H), 7.0 (t, 1H), 6.92 (d,

2H), 5.58 (d, 1H), 5.48 (dd, 1H), ca 5.2 (m, 2H +1H), 5.02 (s, 2H), 4.58 (m, 2H), 1.98 (s, 3H).

EXAMPLE 4

4-Nitrobenzyl 2-[(3R,4R)-4-(p-toluenesulfonylthio)-3-phenoxyacetamido-2-oxo-azetidin-1-yl]-3-methyl-3-butenoate (XIIId)

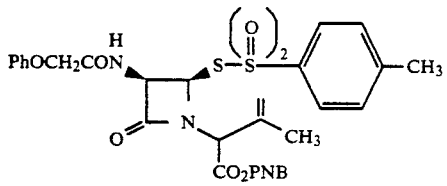

A suspension of 4-nitrobenzyl 2-[(3R,4R)-4-[(benzothiazol-2-yl)dithio]-3-phenoxyacetamido-2-oxo-azetidin-1-yl]-3-methyl-3-butenoate (XIIIc, 3.25 g, 0.005 mole) in acetone (90 mL) and water (10 mL) was treated at room temperature with silver nitrate (1.06 g, 0.00625 mole), followed by treatment with a solution of sodium p-toluenesulfinate hydrate (0.90 g, 0.050 mole) in acetone (70 mL) - water (10 mL). The slurry was stirred for 1 h at room temperature under darkness. It was then filtered through Celite, which was washed with acetone. The volume of the filtrate was reduced in vacuo, and the product was extracted into ether (3×250 mL). The ether phase was dried over magnesium sulfate and concentrated. Flash chromatography (silica gel, 50% ethyl acetate in hexane) gave the pure title product, XIIId, as a solid (2.053 g, 62%).

ANALYTICAL DATA $^1$H-NMR (CDCl$_3$, 360 MHz): δ8.22 (d, 2H), 7.7 (d, 1H), 7.6 (d, 1H), 7.4–7.2 (m, 6H), 7.04 (m, 1H), 7.01 (t, 1H), 6.94 (d, 2H), 5.8 (d, J=5 Hz, 1H), 5.30 (dd, 1H), 5.26 (m, 2H), 4.99 (s, 1H), 4.91 (s, 1H), 4.78 (s, 1H), 4.42 (dd, 2H), 2.38 (s, 3H), 1.92 (s, 3H).

EXAMPLE 5

Diphenylmethyl 2-[(3R,4R)-4-(p-toluenesulfonylthio)-3-phenoxyacetamido-2-oxo-azetidin-1-yl]-3-hydroxy-2-butenoate (XIVa)

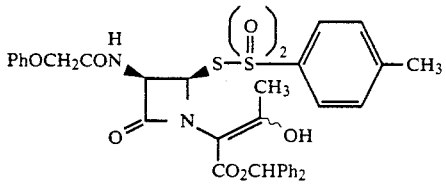

A solution of diphenylmethyl 2-[(3R,4R)-4-(p-toluenesulfonylthio)-3-phenoxyacetamido-2-oxo-azetidin-1-yl]-3-methyl-3-butenoate (XIIIb) (9.00 g, 0.0135 mole) in methyl acetate (250 mL) was cooled to −78° C. and dry ozone was gently bubbled through the solution until a pale blue endpoint was obtained (40 min.). Nitrogen gas was passed through the solution until it became colorless. Subsequently, methylsulfide (15 mL) was added at once, and the solution was allowed to reach 0° C. over the course of 2 h. The crude product, obtained by evaporation of the solvent, was purified by silica gel flash chromatography (50% ethyl acetate in hexane) to yield 8.378 g (91.5%) of the title product as a colorless foam.

ANALYTICAL DATA $^1$H-NMR (CD$_2$Cl$_2$, 360 MHz) δ11.8 (br s, 1H), 7.5–6.9 (m, 19H), 6.85 (s, 1H), 5.75 (d, 1H), 5.1(q, 1H), 4.55 (m, 2H), 2.39 (s, 3H), 2.0 (s, 3H).

EXAMPLE 6

4-Nitrobenzyl 2-[(3R,4R)-4-[(benzothiazol-2-yl)dithio]-3-phenoxyacetamido-2-oxo-azetidin-1-yl]-3-hydroxy-2-butenoate (XIVb)

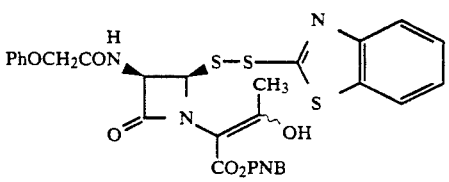

A solution of 4-nitrobenzyl 2-[(3R,4R)-4[(benzothiazol-2-yl)dithio]-3-phenoxyacetamido-2-oxo-azetidin-1-yl]-3-methyl-3-butenoate (XIIIc. 1.52 g 0.00244 mole) in 2:1 methanol/dichloromethane (165 mL), at −78° C., was treated with a stream of dry ozone until a pale blue coloration was reached (10 min). Nitrogen was then bubbled through the solution to discharge the blue color and methyl sulfide (1.5 mL) was added. The solution allowed to reach 0° C. over the course of 2 h. Evaporation of the solvents gave a crude product which was purified by flash-chromatography over silica gel (65% ethyl acetate in hexane) to yield 1.448 g (95%) of the title compound, XIVb, as a white foam.

ANALYTICAL DATA $^1$H-NMR (CDCl$_3$, 360 MHz): δ12.2 (br s, 1H), 8.01 (d, 2H), 7.82 (d, 1H), 7.61 (d, 1H), 7.5–7.2 (m, 7H), 7.01 (t, 1H), 6.98 (d, 2H), 5.39 (d, J=5 Hz, 1H), 5.25–5.0 (m, 3H), 4.6 (m, 2H), 2.36 (s, 3H).

EXAMPLE 7

4-Nitrobenzyl 2-[(3R,4R)-4-(p-toluenesulfonylthio)-3-phenoxyacetamido-2-oxo-azetidin-1-yl]-3-hydroxy-2-butenoate (XIVc)

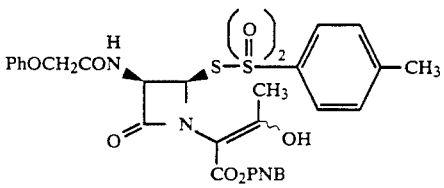

A solution of 4-nitrobenzyl 2-[(3R,4R)-4-(p-toluenesulfonylthio)-3-phenoxyacetamido-2-oxo-azetidin-1-yl]-3-methyl-3-butenoate (XIIId. 1.13 g, 0.00178 mole) in methyl acetate (30 mL) was treated at −78° C. with a slow stream of ozone until a blue coloration persisted (10 min). Nitrogen was used to sweep the excess ozone. Subsequently, methylsulfide (2 mL) was added and the temperature was allowed to reach 0° C. over the course 4 h. Evaporation of the solvent and flash chromatography of the residue (silica gel, 60% ethyl acetate in hexane) gave 1.09 g (96.3%) of the pure title product, XIVc, as a foam.

EXAMPLE 8

Diphenylmethyl 2-[(3R,4R)-4-(p-toluensulfonylthio)-3-phenoxyacetamido-2-oxo-azetidin-1-yl]-3-trifluoromethanesulfonyloxy-2-butenoate (XVa)

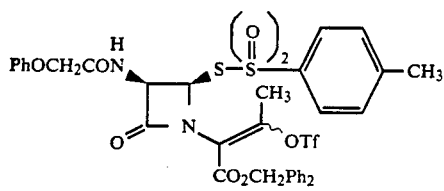

Embodiment a: To a solution of diphenylmethyl 2-[(3R,4R)-4-(p-toluenesulfonylthio)-3-phenoxyacetamido-2-oxo-azetidin-1-yl]-3-hydroxy-2-butenoate (XIVa. 8.35 g, 0.0123 mole) in dry dichloromethane (80 mL), cooled to −78° C., was added triflic (trifluoromethanesulfonic) anhydride (2.60 mL, 0.015 mole) and followed by diisopropylethylamine (2.70 mL, 0.015 mole) rather quickly with vigorous stirring of the solution. After 1 h at −78° C., dilute hydrochloric acid (0.05N, 200 mL) was added and the cooling bath was removed. The product was extracted into ethyl acetate (500 mL). The ethyl acetate phase was first washed twice with dilute hydrochloric acid and then twice with water, dried over magnesium sulfate, and concentrated. Flash silica gel chromatography (40% ethyl acetate in hexane) gave 8.82 g (86.5%) of the title product as a white foam.

ANALYTICAL DATA $^1$H-NMR (CDCl$_3$, 360 MHz) δ7.5-7.0 (m, 18H), 6.98 (s, 1H), 6.82 (d, 2H), 5.90 (d, 1H), 5.00 (dd, 1H), 4.48 (m, 2H), 2.32 (s, 6H).

Embodiment b: To a solution of 4.75 g (7.06 mmol) of diphenylmethyl 2-[(3R,4R)-4-(p-toluenesulfonylthio)-3-phenoxyacetamido-2-oxo-azetidin-1-yl]-3-hydroxy-2-butenoate (XIVa) in 40 mL of dry dichloromethane at −78° C. (dry-ice/acetone) was added, dropwise, 1.53 mL (8.82 mmol) of diisopropylethylamine followed by 1.48 mL (8.82 mmol) of trifluoromethanesulfonic anhydride. The reaction mixture was stirred at −78° C. under an atmosphere of argon for 30 min. After completion of the reaction, as indicated by tlc (thin layer chromatography), the orange solution was quenched with ice-water. The aqueous layer was extracted with dichloromethane (20 mL), and the combined organic layers were washed with brine (10 mL), 10% HCl solution (10 mL), water (5 mL), dried (magnesium sulfate), and concentrated in vacuo to give a yellow colored oil. Flash chromatography of the oil using hexanes-ethyl acetate (1:1) afforded 4.89 g (86%) of the title product as a white foam.

EXAMPLE 9

4-Nitrobenzyl 2-[(3R,4R)-4-[(benzothiazol-2-yl)dithio]-3-phenoxyacetamido-2-oxo-azetidin-1-yl]-3-trifluoromethanesulfonyloxy-2-butenoate (XVb)

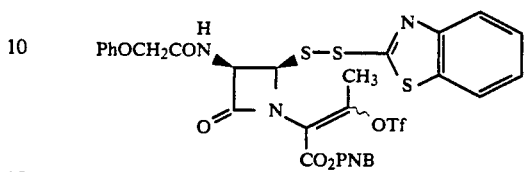

Analogous to a procedure as described in Example 8, 0.144g (0.000230 mole) of 2-[(3R,4R)-4-[(benzothiazol-2-yl)dithio]-3-phenoxyacetamido-2-oxo-azetidin-1-yl]-3-hydroxy-2-butenoate (XIVb), was converted to 0.152 g (87.3%) of the title triflate, XVb, as a white foam after flash chromatography (silica gel, 40% ethyl acetate in hexane).

ANALYTICAL DATA $^1$H-NMR (CDCl$_3$, 360 MHz): δ8.01 (d, 2H), 7.83 (d, 1H), 7.7 (d, 1H), 7.5-7.2 (m, 7H), 7.03 (t, 1H), 6.97 (d, 2H), 5.72 (d, J=5 Hz, 1H), ca. 5 (m, 3H), 4.61 (m, 2H), 2.55 (s, 3H).

MASS (FAB, GLYCEROL): 785 (M$^+$+1)

EXAMPLE 10

4-Nitrobenzyl 2-[(3R,4R)-4-(p-toluenesulfonylthio)-3-phenoxyacetamido-2-oxo-azetidin-1-yl]-3-methanesulfonyloxy-2-butenoate (XVc)

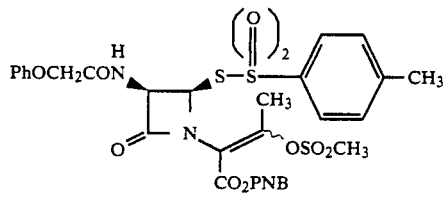

A solution of 4-nitrobenzyl 2-[(3R,4R)-4-(p-toluenesulfonylthio)-3-phenoxyacetamido-2-oxo-azetidin-1-yl]-3-hydroxy-2-butenoate (XIVc. 0.131 g, 0.000206 mole) in dry dichloromethane (3 mL) at −78° C. was treated with triethylamine (0.031 ml, 0.00022 mole) and methanesulfonyl (mesyl) chloride (0.0175 mL, 0.00022 mole), and the temperature was allowed to reach −20° C. over the course of 3 h. Another portion of triethylamine (0.031 mL, 0.00022 mole) and mesyl chloride (0.0175 mL, 0.00022 mole) was added and, after a further 1 h period at −20° C., the brown solution was quenched with dilute hydrochloric acid and extracted with ethyl acetate. The organic phase was washed with dilute acid (0.05N HCl) followed by brine and dried over magnesium sulfate. Flash chromatography (silica gel, 50-60% ethyl acetate in hexane) gave the title product, XVc, as a mixture of E and Z isomers in 1:1 ratio and as a colorless foam. Yield: 0.122 g (83%).

ANALYTICAL DATA $^1$H-NMR (CDCl$_3$, 360 MHz): δ8.25-8.20 (2xdd, 2H), 7.6-6.8 (m, 12 H), 5.95 (d, J=5.3 Hz, 0.5H), 5.90 (d, J=5.3 Hz, 0.5H), 5.33 (m, 2H), 5.18 (dd; J=5.3, 6.5 Hz; 0.5H), 5.05 (dd; J=5.3, 6.5 Hz; 0.5 H), 4.5-4.4 (m, 2H), 3.31 (s, 1.5H), 3.18 (s, 1.5H), 2.6 (s, 1.5 H), 2.42 (s, 1.5H), 2.41 (s, 1.5H), 2.40 (s, 1.5 H).

EXAMPLE 11

Diphenylmethyl 2-[(3R, 4R)-4-[(benzothiazol-2-yl)dithio]-3-phenoxyacetamido-2-oxo-azetidin-1-yl]-3-fluorosulfonyloxy-2-butenoate (XVd)

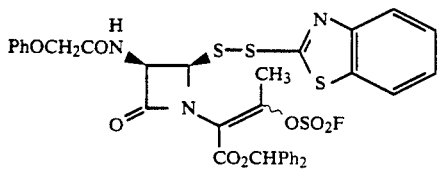

To a solution of 5.0 g (7.32 mmol) of diphenylmethyl 2-[(3R, 4R)-4-[(benzothiazol-2-yl)dithio]-3-phenoxyacetamido-2-oxo-azetidin-1-yl]-3-hydroxy-2-butenoate 20 mL of dry dichloromethane at −78° C. (dry ice/acetone) was added dropwise 1.40 mL (8.05 mmol) of diisopropylethylamine followed by 1.86 mL (10.24 mmol) of fluorosulfonic anhydride. The reaction mixture was stirred at −78° C. under an atmosphere of argon for 2.5 h before quenching with water (50 mL). The organic layer was separated. It was further washed with brine (15 mL), 10% HCl solution (15 mL), and water (15 mL), and dried (magnesium sulfate) and concentrated in vacuo to give a light yellow foam. The foam was further purified by flash chromatography (silica, 45% ethyl acetate in hexanes) to afford 4.6 g (84%) of the title compound.

ANALYTICAL DATA

IR (KBr) 1788, 1733, 1630 cm-1.
$^1$H NMR (CDCl$_3$) δ2.56 (s, 3H), 4.62 (ABq, J=18.9 and 37.8 Hz, 2H), 5.06 (dd, J=5.6 and 7.5 Hz, 1H), 5.57 (d, J=5.6 Hz, 1H), 6.83 (s, 1H), 6.92 (d, J=7.8 Hz, 1H), 6.98-7.83 (m, 19H).
HRMS (high resolution mass spec) calcd for C$_{35}$H$_{28}$FN$_3$O$_8$S$_4$ 766.0822, found 766.0846.

EXAMPLE 12

Diphenylmethyl 2-[(3R, 4R)-4-(p-toluenesulfonylthio)-3-phenoxyacetamido-2-oxo-azetidin-1-yl]-3-fluorosulfonyloxy-2-butenoate (XVe)

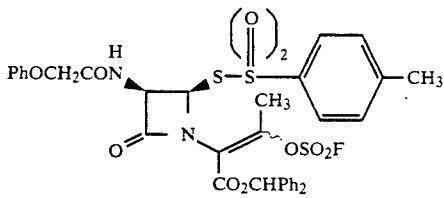

To a solution of 10.0 g (14.86 mmol) of diphenylmethyl 2-[(3R, 4R)-4-(p-tolueneulfonylthio)-3-phenoxyacetamido-2-oxo-azetidin-1-yl]-3-hydroxy-2-butenoate (XIVa) in 90 mL of dry dichloromethane at −78° C. (dry ice/acetone) was added, dropwise, 2.84 mL (16.34 mmol) of diisopropylethylamine followed by 1.69 mL (16.34 mmol) of fluorosulfonic anhydride. The reaction mixture was stirred at −78° C. under an atmosphere of argon for 2.5 h before being quenched with water (50 mL). The organic layer was separated. It was further washed with brine (15 mL), 10% HCl solution (15 mL), and water (15 mL), dried (magnesium sulfate), and concentrated in vacuo to give a light yellow foam. The foam was purified further by flash chromatography (silica, 45% ethyl acetate in hexanes) to afford 9.18 g (82%) of the title product.

ANALYTICAL DATA

IR (KBr) 1795, 1716, 1684 cm-1.
$^1$H NMR (CDCl$_3$) δ2.30 (s, 3H), 2.42 (s, 3H), 4.50 (d, J =2.8 Hz, 2H), 5.05 (dd, J =5.5 and 7.3 Hz, 1H), 5.99 (d, J=5.3 Hz, 1H), 6.88 (d, J=7.8 Hz, 1H), 6.93 (s, 1H), 7.00-7.50 (m, 19H).
HRMS (high resolution mass spec) calcd for C$_{35}$H$_{31}$FN$_2$O$_{10}$S$_3$ 755.1203, found 755.1202.
Anal. Calcd for C$_{35}$H$_{31}$FN$_2$O$_{10}$S$_3$: C, 55.53; H, 4.42; N, 3.70. Found. C, 55.29; H, 4.15; N, 3.63.

EXAMPLE 13

Diphenylmethyl 2-(3R, 4R)-4-(benzothiazol-2-yl)dithiol-3-phenylacetamido-2-oxo-azetidin-1-yl]-3-fluorosulfonyloxy-2-butenoate (XVf)

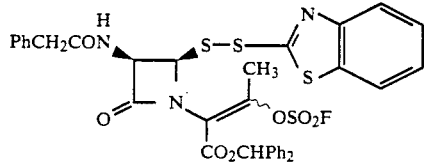

Under a stream of dry nitrogen, the flask was charged with 2.51 g (3.76 mmol) of diphenylmethyl 2-[(3R, 4R)-4-[(benzothiazol-2-yl)dithio]-3-phenylacetamido-2-oxo-azetidin-1-yl]-3-hydroxy-2-butenoate and 45 mL of dry dichloromethane. To the resulting solution at −78° C. was added 0.56 mL (3.95 mmol) of triethylamine followed by 0.41 mL (3.95 mmol) of fluorosulfonic anhydride. After 45 min, the reaction mixture was poured into water (50 mL). The organic phase was separated and washed with water (50 mL) and brine (50 mL). It was further and dried (magnesium sulfate), filtered, and concentrated in vacuo to yield 2.67 g (95%) of the title product as a mixture of Z (major) and E (minor) isomers (6:1).

ANALYTICAL DATA

IR (KBr) 1789, 1718, 1663, cm-1.
$^1$H-NMR (CD$_2$Cl$_2$) (Z-isomer) δ2.54 (s, 3H), 3.72 (s, 2H), 4.87 (dd, J=5.2, and 7.2 Hz, 1H), 5.51 (d, J=5.2, Hz, 1H), 6.28 (d, J=7.2 Hz, 1H), 6.78 (s, 1H), 7.1-7.5 (m, 17H), 7.72 (d, J=7.8 Hz, 1H), 7.84 (d, J =8.1 Hz, 1H);
$^1$H-NMR (CD$_2$Cl$_2$) (E-isomer, partial spectrum) δ2.45 (s, 3H), 3.67 (s, 2H), 5.35 (dd, J=5.0 and 8.0 Hz, 1H), 5.49 (d, J=5.0 Hz, 1H), 6.86 (s, 1H).
HRMS calcd for C$_{35}$H$_{28}$FN$_3$O$_7$S$_4$ 750.0872 (M+H$^+$), found 750.0857.

EXAMPLE 14

Diphenylmethyl 2-[(3R,4R)-4-(p-toluenesulfonylthio)-3-phenoxyacetamido-2-oxo-azetidin-1-yl]-3-p-toluenesulfonyl-2-butenoate (XVg)

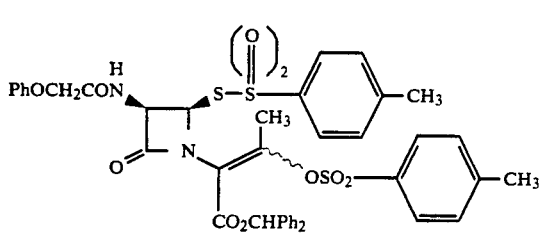

To a solution of 1.0 g (1.48 mmol) of diphenylmethyl 2-[(3R,4R)-4-(p-toluenesulfonylthio)-3-phenoxyacetamido-2-oxo-azetidin-1-yl]-3-hydroxy-2-butenoate (XIVa) was added, dropwise, 283.93 μL (1.63 mmol) of diisopropylethylamine followed by 527.12 mg of p-toluenesulfonic anhydride. The solution was cooled to −78° C. and stirred for 2.0 hr before quenched with ice-water solution (10 mL). The organic layer was separated and washed with water, saturated aqueous NaHCO3 solution, brine and 10% HCl solution. After the solution was further dried (MgSO4) and concentrated, the title compound was isolated as a foam. Further purification by flash chromatography (silica, 50% ethyl acetate in hexanes) afforded 1.04 g (85% yield) of the product. The compound was isolated as a single isomer.

ANALYTICAL DATA

HRMS cacld for $C_{42}H_{39}N_2O_{10}S_3$ 827.1767 (M+H+), found 827.1764.

EXAMPLE 15

2-[(3R,4R)-(p-Toluenesulfonylthio)-3-phenoxyacetamido-2-oxo-azetidin-1-yl]-3-p-nitrobenzenesulfonyloxy-2-butenoate (XVh)

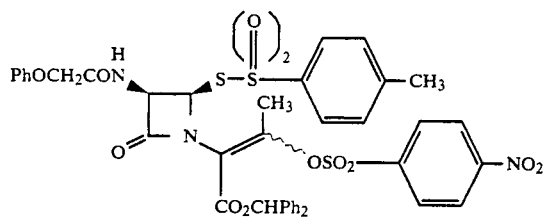

To a solution of 1.0 g (1.48 mmol) of diphenylmethyl 2-[(3R,4R)-4-(p-toluenesulfonylthio)-3-phenoxyacetamido-2-oxo-azetidin-1-yl]-3-hydroxy-2-butenoate (XIVa) in 10 mL dichloromethane at 0° C. was added, dropwise, 246.70 μL (1.77 mmol) of triethylamine followed by 327.9 mg of p-nitrobenzenesulfonyl chloride (1.77 mmol). The reaction mixture was stirred for 2.0 hr at 0° C. before being quenched with an ice-water solution (10 mL). The organic layer was separated and subsequently washed with water, brine, saturated aqueous NaHCO3 solution, and 10% HCl solution. After the solution was further dried (MgSO4) and concentrated, 850 mg (67%) of the title compound was isolated as a yellow foam. The compound was not further characterized but was converted to the correponding allene.

EXAMPLE 16

Diphenylmethyl 2-[(3R,4R)-4-(p-toluenesulfonylthio)-3-phenoxyacetamido-2-oxo-azetidin-1-yl]-2,3-butadienoate (Ia)

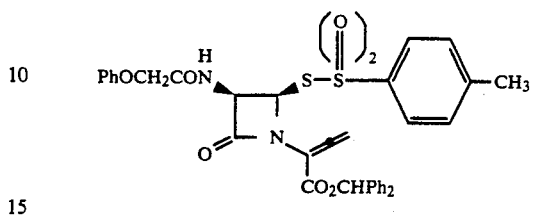

Embodiment a: A solution of diphenylmethyl 2-[(3R,4R)-4-(p-toluenesulfonylthio)-3-phenoxyacetamido-2-oxo-azetidin-1-yl]-3-trifluoromethanesulfonyloxy-2-butenoate (XVa, 0.300 g, 0.00036 mole) in dry tetrahydrofuran (3 mL) was treated with triethylamine (0.077 mL, 0.00036 mole) for 1 h at room temperature. Reverse-phase chromatography (C-18 column, eluting with 65% acetonitrile - 35% of 0.01M phosphate pH 6.5 buffer) showed complete consumption of the starting material after 45 min with formation of a single, faster-eluting product. 0.05M sulfuric acid and ethyl acetate was added to the reaction mixture, followed by separating the two phases The organic phase was dried with sodium sulfate and evaporated to give 0.245g of diphenylmethyl 2-[(3R,4R)-4-(p-toluenesulfonylthio)-3-phenoxyacetamido-2-oxo-azetidin-1-yl]-2,3-butadienoate (Ia) as a colorless foam (quantitative yield)

ANALYTICAL DATA $^1$H NMR (CDCl3) δ2.29 (s, 3H), 4.41 and 4.51 (ABq, J=14.7 and 29.4 Hz, 2H) 5.45 (dd, J=5.0 and 8.4 Hz, 1H), 5.60 (d, J=8.4 Hz, 1H), 6.84 (s, 1H), 6.91 (d, J=8.4 Hz, 1H), 7.03 (t, J=7.5 Hz, 1H), 7.16 (d, J =8.4 Hz, 1H), 7.25–7.41 (m, 16H), 7.60 (d, J=8.4 Hz, 1H).

HRMS calcd for $C_{35}H_{30}N_2O_7S_2$ 655.1573 (M+H+), found 655.1566.

Anal Calcd for $C_{35}H_{30}N_2O_7S_2$: C, 64.27; H, 4.77; N, 4.27. Found C, 64.45; H, 5.07; N, 4.33.

Embodiment b: To a solution of 4.03 g (5.34 mmol) of diphenylmethyl 2-[(3R,4R)-4-(p-toluenesulfonylthio)-3-phenoxyacetamido-2-oxo-azetidin-1-yl]-3-fluorosulfonyloxy-2-butenoate (XVe) in 20 mL of dry dichloromethane at room temperature was added, dropwise, 788.89 μl (5.66 mmol) of triethylamine. The solution was stirred at ambient temperature for 45 min. HPLC indicated a quantitative formation of the product (retention time =2.68 min; 2.0 ml/min flow rate; 60% acetonitrile: 40% of 0.01M (NH4)2HPO4 buffer, pH=6.5, reversed phase C-18 column). The resultant solution was poured into water. The organic layer was separated and washed with brine (10 mL) and 5% HCl solution (10 mL). It was further dried (magnesium sulfate) and concentrated to give a light yellow foam, which was recrystallized from isopropanol to afford 3.15 g (90%) of the title product.

Embodiment c: To a solution of 25 mg (0.03 mmol) of diphenylmethyl 2-[(3R,4R)-4-(p-toluenesulfonylthio)3-phenoxyacetamido-2-oxo-azetidin-1-yl]-3-p-toluenesulfonyl-2-butenoate (XVg) in 1.0 mL of dry dichloromethane at room temperature was added, dropwise, 4.42 μL (0.032 mmol) of triethylamine. The solution was stirred at ambient temperature for 40 min. The reaction mixture was added into water (1.0 mL) and the two phases were separated. The organic layer was washed with brine (2 mL) and 4% HCl solution (2 mL). It was subsequently dried (magnesium sulfate) and concentrated to afford 16.9 mg (87%) of the desired title product.

Embodiment d: To a solution of 600 mg (0.79 mmol) of diphenylmethyl 2-[(3R,4R)-4-(p-toluenesulfonylthio)-3-phenoxyacetamido-2-oxo-azetidin-1-yl]-3-methanesulfonyloxy-2-butenoate (XVc) in 6.0 mL of dichloromethane at room temperature was added 110 µL of triethylamine (0.79 mmol). The solution was stirred for 2.0 hours at ambient temperature. The reaction mixture was added into water (2.0 mL) and the two phases were separated. The organic layer was washed with brine (2 mL), dried (magnesium sulfate) and concentrated to give 445.1 mg (86%) of the desired title product.

Embodiment e: To a solution of 1.0 g (1.24 mmol) of diphenylmethyl 2-[(3R, 4R)-4-(p-toluenesulfonylthio)-3-phenoxyacetamido-2-oxo-azetidin-1-yl]-3-trifluoromethanesulfonyloxy-2-butenoate (XVa) in 10 mL of dichloromethane at room temperature was added triethylamine (0.72 mL, 1.24 mmol). The solution was stirred for 60 min at ambient temperature before being added into water (5.0 mL). The phases were separated. The organic phase was washed with brine (10 mL) and 4% HCl solution (10 mL). It was subsequently dried (magnesium sulfate) and concentrated to afford 0.74 g (90%) of the title product as a foam.

Embodiment f: To a solution of 100 mg (0.11 mmol) of diphenylmethyl 2-[(3R,4R)-(p-toluenesulfonylthio)-3-phenoxyacetamido-2-oxo-azetidin-1-yl]-3-p-nitrobenzenesulfonyloxy-2-butenoate (XVh) in 2.0 mL of dichloromethane at room temperature was added triethylamine (15.49 µl, 0.11 mmol). The solution was stirred at ambient temperature for 45 min before being added into water (2.0 mL). The phases were separated. The organic phase was washed with brine (2 mL) and 4% HCl solution (2 mL). It was subsequently dried (magnesium sulfate) and concentrated to give the title product (62.7 mg, 87%).

EXAMPLE 17

Diphenylmethyl 2-[(3R, 4R)-4-[(benzothiazol-2-yl)dithio]-3-phenoxyacetamido-2-oxo-azetidin-1-yl]-2,3-butadienoate (Ib)

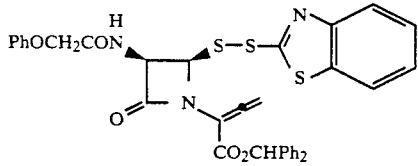

Embodiment a: To a solution of 200 mg (0.261 mmol) of diphenylmethyl 2-[(3R, 4R)-4-[(benzothiazol-2yl)dithio]-3-phenoxyacetamido-2-oxo-azetidin-1-yl]-3-fluorosulfonyloxy-2-butenoate (XVd) in 2.0 mL of dry dichloromethane at room temperature was added, dropwise, 38.26 µL (0.274 mmol) of triethylamine. The solution was stirred at ambient temperature for 25 min. HPLC indicated disappearance of the starting material and formation of the product (retention time =4.74 min, 2.0 mL/min, 70% acetonitrile: 30% water, reversed phase C-18 column). The resultant solution was poured into water. The organic layer was separated and further washed with brine (10 mL) and 5% HCl solution (10 mL). It was subsequently dried (magnesium sulfate) and concentrated to give 139.09 mg (81%) of the title product as a light brown foam, which was further purified by recrystallization from isopropanol.

ANALYTICAL DATA $^1$H NMR (CDCl$_3$) δ4.41 and 4.49 (ABq, J=17.0 and 29.3 Hz, 2H), 5.120 (d, J=15.5 Hz, 1H), 5.60 (dd, J=5.0 and 8.0 Hz, 1H), 5.65 (d, J=15.5 Hz, 1H), 6.83 (s, 1H), 7.60–6.90 (m, 18H), 7.82 (d, J=9.5 Hz, 1H).

Embodiment b: To a solution of 20 mg (0.03 mmol) of diphenylmethyl 2-[(3R, 4R)-4-[(benzothiazol-2-yl)dithio]-3-phenoxyacetamido-2-oxo-azetidin-1-yl]-3-methanesulfonyloxy-2-butenoate in 2.0 mL of dichloromethane at room temperature was added 4.39 µL (0.031 mmol) of triethylamine. The solution was stirred at ambient temperature for 40 min. The reaction mixture was added into water (1.0 mL) and phases were separated. The organic layer was washed with brine (2 mL) and 4% HCl solution (2 mL). It was subsequently dried (magnesium sulfate) and concentrated to afford 14.2 mg (82%) of the title product.

Embodiment c: A solution of diphenylmethyl 2-[(3R, 4R)-4-[(benzothiazol-2-yl)dithio]-3-phenoxyacetamido-2-oxo-azetidin-1-yl]-3-trifluoromethanesulfonyloxy-2-butenoate (49 mg, 0.06 mmol) in deuterodichloromethane (0.4 mL) was treated with triethylamine (8.4 mL, 0.06 mmol) at room temperature. After a period of 45 minutes, NMR and reverse-phase HPLC indicated consumption of the starting material with formation of a single peak at retention time=4.74 (C-18, 2.0 mL/min, 70% acetonitrile and 30% water). The reaction was stopped by pouring the mixture into water (2.0 mL). The aqueous layer was extracted with dichloromethane (2.0 mL) and dried (magnesium sulfate). The title product is stable in solution, however, any attempts to isolate the allenylazetidinone ended up in its decomposition.

EXAMPLE 18

Diphenylmethyl 2-[(3R, 4R)-4-[(benzothiazol-2-yl)dithio]-3-phenylacetamido-2-azetidinon-1-yl]-2,3-butadienoate (Ic)

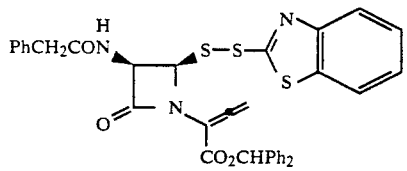

Under a stream of dry nitrogen, the flask was charged with 500 mg (0.65 mmol) of diphenylmethyl 2-[(3R, 4R)-4-[(benzothiazol-2-yl)dithio]-3-phenylacetamido-2-oxo-azetidin-1-yl]-3-fluorosulfonyloxy-2-butenoate (XVf) and 5.0 mL of dry THF. After stirring the solution for 15 min at 0°–5° C., 92.0 µL (0.65 mmol) of triethylamine was added dropwise. Stirring at 0°–5° C. under a blanket of dry nitrogen was continued for 2 h. The solution was diluted with THF (10 mL) and poured into an aqueous saturated NaCl solution (30 mL). The phases were separated and the organic phase was dried 15 min over anhydrous MgSO$_4$, filtered and concentrated to a small volume (ca. 6 mL). The solution was added dropwise into 36 mL of hexanes with vigorous stirring. After 30 min, the solid was collected by suction filtration and dried in vacuo for 3 h at 22° C. to yield 387 mg (92%) of the title product as a beige powder.

ANALYTICAL DATA $^1$H NMR (CD$_2$Cl$_2$) δ3.65 (s, 2H), 5.20 and 5.59 (ABq, J=15.3 Hz, 2H), 5.41 (dd, J=4.8 and 8.0 Hz, 1H), 5.76 (d, J=4.8 Hz, 1H), 6.51 (d, J=8 Hz, 1H), 6.78 (s, 1H), 7.0-7.5 (m, 17H), 7.52 (d, J=7.9 Hz, 1H), 7.81 (d, J=8.4 Hz, 1H).

HRMS calcd for C$_{35}$H$_{27}$N$_3$O$_4$S$_3$ 650.1242, found 650.1244 (M+H+).

EXAMPLE 19

4-Nitrobenzyl 2-[(3R,4R)-4-[(benzothiazol-2-yl)dithio3-phenoxyacetamido-2-oxo-azetidin-1-yl]-2,3-butadienoate (Id)

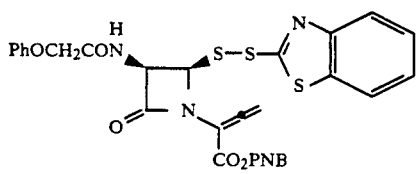

A solution of 4-nitrobenzyl 2-[(3R4R)-4-[(benzothiazol-2-yl)dithio]-3-phenoxyacetamido-2-oxo-azetidin-1-yl]-3-trifluoromethanesulfonyloxy-2-butenoate (XVb, 0.147 g, 0.000187 mole) in acetonitrile at −40° C. was treated with triethylamine (0.026 mL, 0.000187 mole). A tan precipitate formed. The temperature of the mixture was allowed to reach −10° C. over the course of 1 h, and the suspension was carefully filtered under argon atmosphere. The precipitate was washed with ice-cold acetonitrile (2×2 mL). After drying the solid in vacuo for 30 min at room temperature, the 0.070g (59% yield) of the title allenylazetidinone, Id, was obtained. It could be stored at −10° C. for several days, but it was preferably used within 24 h of its preparation.

ANALYTICAL DATA $^1$H-NMR (CDCl$_3$, 360 MHz): δ8.15 (d, 2H), 7.82 (d, 1H), 7.62 (d, 1H), 7.51 (d, 1H), 7.5-7.2 (m, 6H), 7.0 (t, 1H), 6.94 (d, 2H), 5.80 (d, J=5 Hz, 1H), 5.6 (d+dd, 2H), 5.34 (d, J=17.5 Hz, 1H), 5.12 (dd, 2H), 4.58 (dd, 2H).

IR (KBr cast): cm$^{-1}$ 1950; 1910 (weak).

EXAMPLE 20

4-Nitrobenzyl 2-[(3R,4R)-4-(p-toluenesulfonylthio)-3-phenoxyacetamido-2-oxo-azetidin-1-yl]-2,3-butadienoate (Ie)

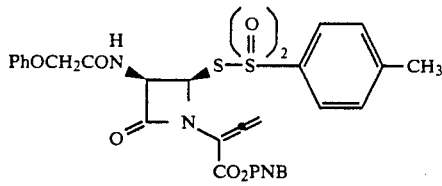

A solution of 4-nitrobenzyl 2-[(3R,4R)-4-(p-toluenesulfonylthio)-3-phenoxyacetamido-2-oxo-azetidin-1-yl]-3-methanesulfonyloxy-2-butenoate (XVc, 0.0714 g, 0.00010 mole) in chloroform (1 mL) was treated with triethylamine (0.014 mL, 0.00010 mole) at room temperature. After a period of 1 h, reverse-phase C-18 HPLC indicated consumption of the starting material with formation of a single new peak (eluting phase:

65% acetonitrile and 35% 0.01M phosphate pH 6.5 buffer). Dilute hydrochloric acid (chilled at 0° C.) and ethyl acetate were added. The organic layer was washed with cold water, dried (sodium sulfate) and concentrated to give 0.0615 g (ca. 100%) of the title compound as a foam. The product was characterized by its $^1$H-NMR spectrum.

ANALYTICAL DATA $^1$H-NMR (CDCl$_3$, 360 MHz): δ8.21 (d, 2H), 7.71 (d, 1H), 7.55 (d, 1H), 7.35-7.25 (m, 7H), 7.02 (t, 1H), 6.89 (d, 2H), 5.94 (d, J=5.5 Hz, 1H), 5.80-5.70 (2d's, J=ca. 17.5 Hz, 2H), 5.53 (dd; J=5.5, 7.0 Hz; 1H), 5.32 (m, 2H), 4.45 (m, 2H), 2.40 (s, 3H).

EXAMPLE 21

Diphenylmethyl 7-phenoxyacetamido-3-methylceph-3-em-4-carboxylate (IIa)

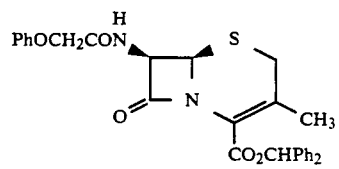

Embodiment a: An oven dried flask containing copper iodide (92.9 mg, 0.48 mmol), previously dried in an Abderholden apparatus, was purged with argon four times. THF (2.0 mL) was added via syringe and the resulting slurry was cooled to −78° C. (acetone/dry ice) before dropwise addition of methylmagnesium bromide (0.32 mL, 0.97 mmol, 3.0M solution in ether). The mixture was then warmed by removing the cooling bath until CuI dissolved forming a homogeneous grey solution and then re-cooled to −78° C. A solution of diphenylmethyl 2-[(3R, 4R)-4-(p-toluenesulfonylthio)-3-phenoxyacetamido-2-oxo-azetidin-1-yl]-2,3-butadienoate (Ia) (200 mg, 0.30 mmol, dissolved in 1.0 mL of THF) was added dropwise to the cuprate slurry. The reaction was stirred for 15 min and quenched with a saturated aqueous ammonium chloride solution. The aqueous phase was extracted with ethyl acetate (15 mL). The organic layer was washed with brine (10 mL)and 10% sodium bicarbonate (10 mL), dried (magnesium sulfate) and concentrated in vacuo to a thick oil. Further purification by silica gel flash chromatography (40% ethyl acetate in hexanes) provided 144.5 mg (92%) of the desired cephem.

ANALYTICAL DATA

IR (KBr) 1780, 1722, 1683 cm-1.

$^1$H NMR (CDCl$_3$) δ2.12 (s, 3H), 3.20 and 3.45 (ABq, J=19.0 Hz, 2H), 5.05 (d, J=5.05 Hz, 1H), 5.9 (dd, J=5.0 and 9.8 Hz, 1H), 7.52-6.91 (m, 16H)

Anal. Calcd for C$_{29}$H$_{26}$N$_2$O$_5$S: C, 67.49; H, 5.09; N, 5.44. Found. C, 67.55; H, 5.09; N, 5.40.

Embodiment b: In a two necked flask, copper cyanide (69.14 mg, 0.77 mmol) was placed. One outlet of the flask was connected to nitrogen, while the other outlet was closed using a rubber septum. The flask was evacuated 2 times and purged with nitrogen. A postive pressure of nitrogen was maintained throughout the reaction. Using a syringe, dry tetrahydrofuran (3 mL) was delivered and the flask was cooled to 0° C. (ice bath).

To the stirred solution was added, a 1.29M solution of methyl lithium in hexane (1.19 mL, 1.54 mmol) dropwise, and the solution was stirred for 20 minutes without an ice bath. The clear homogeneous solution of dimethyl cyano cuprate was cooled to −78° C. (acetone-dry ice), and to the stirred solution was then added a solution of diphenylmethyl-2-[(3R, 4R)-4-(p-toluenesulfonylthio)-3 -phenoxyacetamido-2-oxo-azetidin-1-yl]-2,3-butadienoate (Ia) (0.30 mmol) in tetrahydrofuran. The reaction was stirred for additional 60 minutes at −20° C. (dry ice-carbon tetrachloride) before been quenched with a saturated aqueous ammonium chloride solution (10 mL). The aqueous layer was extracted with ethyl acetate (10×2 mL), and the organic phase was dried (magnesium sulfate) and concentrated to give a yellow oil. The crude reaction mixture was subjected to chromatography (silica, 30% ethyl acetate in hexanes) to give 64.7 mg (42%) of the title product, Ia, and 35.4 mg (21%) of Δ-2 isomer, diphenylmethyl 7-phenoxyacetamido-3-methyl-2-cephem-4-carboxylate.

ANALYTICAL DATA

1-NMR (CDCl$_3$, 360 MHz): Diphenylmethyl 7-phenoxyacetamido-3-methyl-2-cephem-4-carboxylate, δ7.52-6.91 (m, 16H), 5.94 (s, 1H), 5.70 (dd, J=5.0 and 9.8 Hz, 1H), 5.28 (d, J=5.0 Hz, 1H), 4.86 (s, 1H), 4.55 (s, 2H), 1.80 (s, 3H).

EXAMPLE 22

Diphenylmethyl 7-phenoxyacetamido-3-ethylceph-3-em-4-carboxylate (IIb)

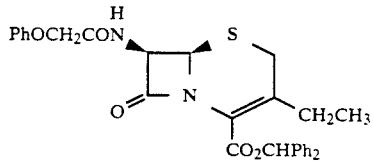

Using the representative procedure as described in Example 21, diethylcuprate [prepared from copper iodide (43.59 mg, 0.23 mmol) and ethylmagnesium bromide (0.16 mL, 0.46 mmol, 3.0M solution)] on reacting with allenylazetidinone Ia (100 mg, 0.15 mmol) provided 68.52mg of diphenylmethyl 7-phenoxyacetamido-3-ethylceph-3-em-4-carboxylate (IIb) (85% yield).

ANALYTICAL DATA

IR (KBr) 1781, 1723, 1690 cm-1.

$^1$H NMR (CDCl$_3$) δ1.05 (t, J=8.5 Hz, 3H), 2.20 (m, 1H), 2.60 (m, 1H), 3.26 and 3.40 (ABq, J=18.9 Hz, 2H), 4.55 (s, 2H), 5.0 (d, J=5.0 Hz, 1H), 5.83 (dd, J=5.0 and 9.8 Hz, 1H), 7.41-6.90 (m, 17H).

Anal. Calcd for C$_{30}$H$_{28}$N$_2$O$_5$S: C, 68.16; H, 5.34; N, 5.30. Found. C, 68.15; H, 5.27; N, 5.36.

EXAMPLE 23

Diphenylmethyl 7-phenoxyacetamido-3-isopropylceph-3-em-4-carboxylate (IIc)

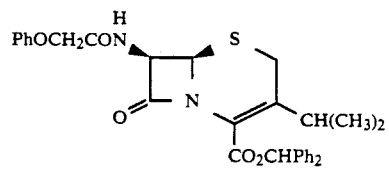

Using the representative procedure as described in Example 21, diisopropylcuprate [prepared from copper iodide (86.98 mg, 0.46 mmol) and isopropylmagnesium chloride (0.45 mL, 0.92 mmol, 2.0M solution)] on reacting with allenylazetidinone Ia (200 mg, 0.31 mmol) provided 126.98 mg of diphenylmethyl phenoxyacetamido-3-isopropylceph-3-em-4-carboxylate (IIc) (78% yield).

ANALYTICAL DATA

IR (KBr) 1780, 1723, 1687 cm-1.

$^1$H NMR (CDCl$_3$) δ0.97 (d, J=7.0 Hz, 3H), 1.05 (d, J=7.0 Hz, 3H), 3.17-3.40 (m, 3H), 4.55 (s, 2H), 5.0 (d, J=4.8 Hz, 1H), 5.82 (dd, J=4.8 and 9.5 Hz, 1H), 6.89-7.05 (m, 3H), 7.20-7.40 (m, 14H).

Anal. Calcd for C$_{31}$H$_{30}$N$_2$O$_5$S: C, 68.62; H, 5.57; N, 5.16. Found. C, 68.78; H, 5.53; N, 5.14.

EXAMPLE 24

Diphenylmethyl 7-phenoxyacetamido-3-n-butylceph-3-em-4-carboxylate (IId)

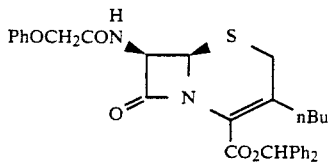

Using the representative procedure as decribed in Example 21, n-dibutylcuprate [prepared from copper iodide (43.59 mg, 0.23 mmol) and n-butylmagnesium bromide (0.22 mL, 0.46 mmol, 2.0M solution)] on reacting with allenylazetidinone Ia (100 mg, 0.15 mmol) provided 76.32 mg of diphenylmethyl 7-phenoxyacetamido-3-n-butylceph-3-em-4-carboxylate (IId) (89%).

ANALYTICAL DATA

IR (KBr) 1777, 1723, 1690 cm$^{-1}$.

$^1$H NMR (CDCl$_3$) d 0.94-1.91 (m, 10H), 2.92 (br t, 1H), 3.24 and 3.37 (ABq, J=18.9 Hz, 2H), 4.55 (s, 2H), 5.0 (d, J=4.8 Hz, 1H), 5.80 (dd, J=4.8 and 9.5 Hz, 1H), 6.90-7.40 (m, 17H).

Anal. Calcd for C$_{34}$H$_{34}$N$_2$O$_5$S: C, 70.08; H, 5.88; N, 4.80. Found. C, 70.04; H, 6.00; N, 4.72.

EXAMPLE 25

Diphenylmethyl 7-phenoxyacetamido-3-t-butylceph-3-em-4-carboxylate (IIe)

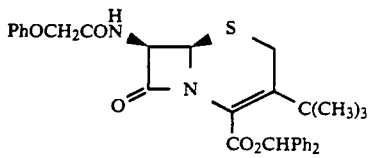

Using the representative procedure as described in Example 21, di-t-butylcuprate [prepared from copper iodide (86.98 mg, 0.46 mmol) and t-butylmagnesium bromide (0.45 mL, 0.92 mmol, 2.0M solution)] on reacting with allenylazetidinone Ia (200 mg, 0.31 mmol) provided 134.59 mg of diphenylmethyl 7-phenoxyacetamido-3-t-butylceph-3-em-4-carboxylate (IIe) (78% yield).

ANALYTICAL DATA

IR (KBr) 1777, 1721, 1680 cm$^{-1}$.

$^1$H NMR (CDCl$_3$) $\delta$1.05 (s, 9H), 3.30 and 3.45 (ABq, J=18.9 Hz, 2H), 4.35 (s, 2H), 4.95 (d, J=4.8 Hz, 1H), 5.83 (dd, J=4.8 and 9.5 Hz, 1H), 6.91 (d, J=9.5 Hz, 1H), 7.02 (s, 1H), 7.20-7.40 (m, 15H).

EXAMPLE 26

Diphenylmethyl 7-phenoxyacetamido-3-hexylceph-3-em-4-carboxylate (IIf)

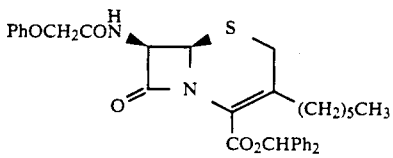

Using the representative procedure as described in Example 21, dihexylcuprate [prepared from copper bromide dimethyl sulfide complex (395.7 mg, 1.92 mmol) and hexylmagnesium bromide (1.92 mL, 3.84 mmol, 2.0M solution] on reacting with allenylazetidinone Ia (629 mg, 0.96 mmol) provided 438 mg of diphenylmethyl 7-phenoxyacetamido-3-hexylceph-3-em-4-carboxylate (IIf) (78% yield).

ANALYTICAL DATA

IR (KBr) 1773, 1722, 1687 cm$^{-1}$.

$^1$H NMR (CDCl$_3$) $\delta$0.87 (t, J=7.5 Hz, 3H), 0.94-1.60 (m., 8H), 2.26 (m, 1H), 2.47 (m, 1H), 3.24 and 3.40 (ABq, J=18.9 Hz, 2H), 4.55 (s, 2H), 5.0 (d, J=4.8 Hz, 1H), 5.84 (dd, J=4.8 and 9.5 Hz, 1H), 6.80-7.45 (m, 17 H).

Anal Calcd for C$_{34}$H$_{36}$N$_2$O$_5$S: C, 69.84; H, 6.20; N, 4.79. Found. C, 69.44; H, 6.22; N, 4.71.

EXAMPLE 27

Diphenylmethyl 7-phenoxyacetamido-3-phenylceph-3-em-4-carboxylate (IIq)

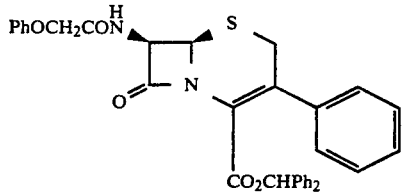

Using the reprentative procedure as described in Example 21, diphenyl cuprate [prepared from copper iodide (92.9 mg, 0.49 mmol) and phenylmagnesium bromide (0.98 mL, 0.98 mmol, 1.0M solution] on reacting with allenylazetidinone Ia (200 mg, 0.31 mmol) provided 128.4 mg of diphenylmethyl 7-phenoxyacetamido-3-phenylceph-3-em-4-carboxylate (IIg) (75% yield).

ANALYTICAL DATA

IR (KBr) 1772, 1720, 1690 cm-1.

$^1$H NMR (CDCl$_3$) $\delta$3.62 (s, 2H), 4.58 (s, 2H), 5.10 (d, J =5.0 Hz, 1H), 5.96 (dd, J=5.1 and 9.8 Hz, 1H), 6.81-7.36 (m, 22H).

EXAMPLE 28

Diphenylmethyl 7-phenoxyacetamido-3-cyclohexylceph-3-em-4-carboxylate (IIh)

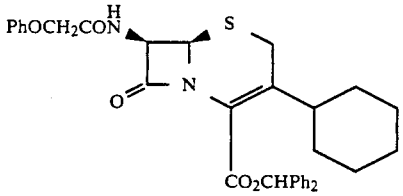

Using the representative procedure as described in Example 21, dicyclohexylcuprate [prepared from copper iodide (85.69 mg, 0.45 mmol) and cyclohexylmagnesium chloride (0.45 mL, 0.90 mmol, 2.0M solution)] on reacting with allenylazetidinone Ia (200 mg, 0.31 mmol) afforded 135.47 mg of diphenylmethyl 7-phenoxyacetamido-3-cyclohexylceph-3-em-4-carboxylate (IIh) (75% yield).

ANALYTICAL DATA

IR (KBr) 1777, 1723, 1690 cm-1.

$^1$H NMR (CDCl$_3$) $\delta$0.94-1.91 (m, 10 H), 2.92 (brt, 1H), 3.24 and 3.37 (ABq, J=18.9 Hz, 2H), 4.55 (s, 2H), 5.0 (d, J=4.8 Hz, 1H), 5.80 (dd, J=4.8 and 9.5 Hz, 1H), 6.90-7.40 (m, 17 H).

Anal. Calcd for C$_{34}$H$_{34}$N$_2$O$_5$S: C, 70.08; H, 5.88; N, 4.80 Found. C, 70.04; H, 6.00; N, 4.72.

EXAMPLE 29

Diphenylmethyl 7-phenoxyacetamido-3-cyclopentylceph-3-em-4-carboxylate (IIi)

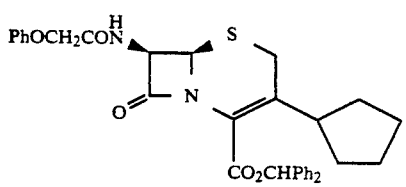

Using the representative procedure as described in Example 21, dicyclopentylcuprate [prepared from copper bromide-dimethyl sulfide complex (316.6 mg, 1.54 mmol) and cyclopentylmagnesium chloride (1.54 mmol, 3.08 mmol, 2.0M solution )] on reacting with allenylazetidinone Ia (504.5 mg. 0.77 mmol) afforded 297.74 mg of diphenylmethyl 7-phenoxyacetamido-3-cyclopentylceph-3-em-4-carboxylate (IIi) (68% yield).

ANALYTICAL DATA

IR (KBr) 1778, 1723, 1685 cm$^{-1}$.

$^1$H NMR (CDCl$_3$) δ1.21-1.92 (m, 8H), 3.10-3.40 (m, 3H), 4.53 (s, 2H), 5.02 (d, J=4.8 Hz, 1H), 5.80 (dd, J=4.8 and 9.5 Hz), 6.90-7.08 (m, 3H), 7.20-7.45(m, 14H).

Anal. Calcd for C$_{33}$H$_{32}$N$_2$O$_5$S: C, 69.69; H, 5.67; N, 4.93.

Found. C, 69.34; H, 5.67; H, 4.83.

EXAMPLE 30

Diphenylmethyl 7-phenoxyacetamido-3-vinylceph-3-em-4-carboxylate (IIj)

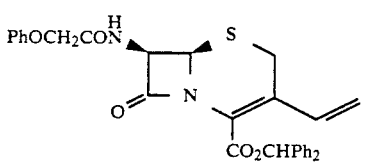

Using the representative procedure as described in Example 21, divinylcuprate [prepared from copper iodide (63.93 mg, 0.34 mmol) and vinylmagnesium bromide (0.67 mL, 0.67 mmol, 1.0M solution) on reacting with allenylazetidinone Ia (100 mg, 0.15 mmol) provided 62.67 mg of diphenylmethyl 7-phenoxyacetamido-3-vinylceph-3-em-4-carboxylate (IIj) (78% yield).

ANALYTICAL DATA

IR (KBr) 1781, 1723, 1680 cm$^{-1}$.

$^1$H NMR (CDCl$_3$) δ3.47 and 3.62 (ABq, J=17.8 Hz, 2H), 4.55 (s, 2H), 5.05 (d, J=4.8 Hz, 1H), 5.62 (d, J=11.2 Hz, 1H), 5.41 (d, J=17.2 Hz, 1H), 5.90 (dd, J=4.8 and 9.5 Hz, 1H), 6.83-7.44 (m, 17H).

Anal Calcd for C$_{30}$H$_{26}$N$_2$O$_5$S.0.42 H$_2$O: C, 67.45; H, 4.90; N, 5.24. Found. C, 67.45; H, 5.02; N, 5.35.

EXAMPLE 31

Diphenylmethyl 7-phenoxyacetamido-3-allylceph-3-em-4-carboxylate (IIk)

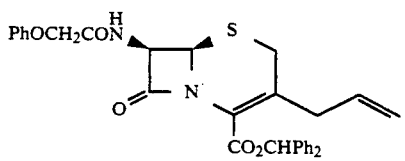

Using the representative procedure as described in Example 21, diallylcuprate [prepared from copper iodide (63.93 mg, 0.33 mmol) and allylmagnesium bromide (0.67 mL, 0.67 mmol, 1.0M solution in ether)] on reacting with allenylazetidinone Ia (100 mg, 0.15 mmol) afforded 67.57 mg of the desired cephem (IIk) (82% yield).

ANALYTICAL DATA

1H NMR (CDCl$_3$) δ2.86 (dd, J=7.5 and 14.2 Hz, 1H), 3.24-3.44 (m, 3H), 4.56 (s, 2H), 4.91-5.18 (m, 3H), 5.60-5.80 (m, 1H), 5.89 (dd, J=7.5 and 14.0 Hz, 1H), 6.89 (d, J=7.5 and 14.0 Hz, 1H), 6.89 (d, J=8.5 Hz, 1H), 6.95 (s, 1H), 7.05 (t, J=7.5 Hz, 1H), 7.20-7.41 (m, 14H).

EXAMPLE 32

Diphenylmethyl 7-phenoxyacetamido-3-Z-propenylceph-3-em-4-carboxylate (IIm)

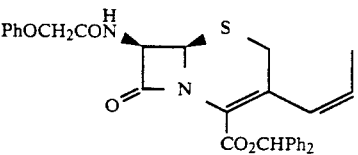

Embodiment a: In a two necked flask under argon atmosphere was placed copper iodide (348.50 mg, 1.83 mmol). The flask was evacuated and purged with argon three times. Using a syringe, freshly distilled THF (15.0 mL) was added. The suspension was cooled to −78° C. (dry ice/acetone). To the stirred suspension at −78° C. was added Z-propenyl magnesium bromide [prepared according to the method decribed by Whiteside, et al., in the *Journal of the American Chemical Society* 93, p. 1379 (1971); 3.66 mmol in 4.81 mL of THF, containing <4% of the E isomer] over a period of 5.0 min. The dry ice/acetone bath was removed and the suspension was stirred for 20 min (a black homogeneous thick slurry was observed). The organocuprate solution was re-cooled to −78° C. and to it was added dropwise the solution of allenylazetidinone Ia (1.0 g, 1.53 mmol, dissolved in 5.0 mL of THF). After 15 min, HPLC indicated disappearance of the allenylazetidinone and formation of a product. The reaction was stopped by quenching it with a saturated aqueous ammonium chloride solution (30 mL). The aqueous layer was extracted with ethyl acetate (20 mL). The organic layer was further washed with brine (15 mL), 10% NaHCO$_3$ solution (15 mL) and water (15 mL), dried (MgSO4) and concentrated to give a yellow foam. After the foam was triturated with hot isopropanol, 499 mg (61% yield) of the desired title product crystallized out as a yellow amorphous powder (HPLC indicated <4% of the E isomer).

ANALYTICAL DATA

IR (KBr) 1779, 1728, 1633 cm-1.

$^1$H NMR (CDCl$_3$) d 1.43 (d, J=7.0 Hz, 3H), 3.27 and 3.47 (ABq, J=17.5 Hz, 2H), 4.58 (s, 2H), 5.07 (d, J =4.5 Hz, 1H), 5.56 (m, 1H), 5.90 (dd, J=4.5 and 9.8 Hz, 1H), 6.10 (d, J=11.7 Hz, 1H), 6.90-7.51 (m, 17H).

Anal. Calcd for C$_{31}$H$_{28}$N$_2$O$_5$S: C, 68.87; H, 5.22; N, 5.18. Found. C, 69.49; H, 5.23, N, 5.22.

Embodiment b: The HPLC indicated that higher yield was achieved when the reaction as described in the above Embodiment (a) between the organo-copper reagent, derived from copper iodide and Z-propenylmagnesium chloride, with allenylazetidinone Ia was run at −100° C.

Embodiment c: In a two necked flask, under nitrogen atmosphere, was placed copper iodide (34.2 mg, 0.18 mmol) followed by THF (3.0 mL) and Z-1-propenyl tri-n-butyl-stannane (119.5 mg, 0.36 mmol). The flask was cooled to −78° C. and 1.6M solution of n-butyllithium in hexanes (0.23 mL, 0.36 mmol) was added dropwise. After stirring the reaction mixture for 3.0 hours at −78° C., a solution of diphenylmethyl 2-[(3R, 4R)-4-[(benzothiazol-2-yl)dithio]-3-phenoxyacetamido-2-oxo-azetidin-1-yl]-2,3-butadienoate (Ib) [prepared in-situ from the corresponding triflate, 49 mg, 0.06 mmol in 0.4 mL of CH$_2$Cl$_2$, and triethylamine (8.4 µl, 0.06 mmol)] was added slowly. The cooling-bath was removed and the reaction mixture was stirred for 60 min before the reaction was quenched with an aqueous saturated solution of ammonium chloride. The aqueous layer was extracted with dichloromethane (10 mL). The organic layer was washed with brine (10 mL) and 10% NaHCO3 (10 mL), dried (magnesium sulfate) and concentrated to give a brown oil. After flash chromatography (silica, 40% ethyl acetates in hexanes), 17.8 mg of the pure title cephem was isolated (55% yield). The spectroscopic data was consistent with the structure.

Embodiment d: In a two necked flask under nitrogen atmosphere was placed copper cyanide (72.54 mg, 0.81 mmol) followed by THF (1.5 mL) and Z-1-propenyl tri-n-butylstannane (537.98 mg, 1.62 mmol). The flask was cooled to 0° C. and 1.4M methyl lithium solution in hexanes (1.15 mL, 1.62 mmol) was added dropwise. Ice bath was removed and the clear solution was stirred for 3.0 h. The flask was re-cooled to −78° C. and a solution of allenylazetidinone Ia or Ib [each prepared from the corresponding triflate (0.32 mmol dissolved in 2.0 mL of CH$_2$Cl$_2$) and triethylamine (53 µL, 0.32 mmol)] was added slowly. The ice bath was removed and the mixture was stirred for additional 60 min before the reaction was quenched with an aqueous saturated ammonium chloride solution (10 mL). The aqueous layer was extracted with ethyl acetate (10 mL). The organic layer was washed with brine (5 mL) and 10% NaHCO3 solution (5 mL), dried (magnesium sulfate) and concentrated to a yellow oil. Further purification by flash chromatography (40% ethyl acetate in hexanes) afforded an inseparable isomeric mixture (2:1) of diphenylmethyl 7-phenoxyacetamido -3-Z-propenyl-ceph-3-em-4-carboxylate (IIm) and 7-phenoxyacetamido 3-Z-propenylceph-2-em-4-carboxylate [Yield: 69.12 mg (45%) from allenylazetidinone Ia; 51 mg (33%) from allenylazetidinone Ib.]

ANALYTICAL DATA $^1$H NMR (CDCl$_3$) (diphenylmethyl 7-phenoxyacetamido-3-Z-propenylceph-2-em-4-carboxylate) δ1.62 (d, J=7.0 Hz, 3H), 4.58 (s, 2H), 4.92 (s,1H), 5.33 (d, J= 4.05 Hz, 1H), 5.56 (m, 1H), 5.71 (m, 2H), 6.10 (s, 1H), 6.90-7.51 (m, 17H).

Embodiment e: In a two necked flask, under argon atmosphere, was placed copper iodide (93.31 mg, 0.49 mmol) followed by THF (2.0 mL). The flask was cooled to −78° C. and Z-propenyllithium (1.0 mL, 0.98 mmol, 0.98M solution in ether) was added dropwise. The cooling-bath was removed and the suspension was stirred for 15 min. The black colored cuprate solution was recooled to −78° C. Slowly via a syringe, a solution of allenylazetidinone Ia or Ib (0.196 mmol in 1.0 mL of THF) was added. The reaction mixture was stirred at −78° C. for 30 min before the reaction was quenched with a solution of saturated aqueous ammonium chloride. The aqueous layer was extracted with ethyl acetate (5 mL). The organic layer was washed with brine (3 mL) and 10% NaHCO3 solution (5 mL), dried (magnesium sulfate), and concentrated to give a yellow colored oil. Further purification using flash chromatography (silica, 40% ethyl acetate in hexanes) afforded 65.6 mg (60%) of the title cephem from allenylazetidinone Ia or 55.7mg (51%) from allenylazetidinone Ib.

Embodiment f: In a two necked flask under an argon atmosphere was placed copper cyanide (43.86 mg, 0.49 mmol) and THF (4.0 mL). The flask was cooled to −78° C. and Z-propenyllithium (0.49 mL, 0.49 mmol), followed by methyllithium (0.24 mL, 0.49 mmol, 2.0M solution in ether), was added. The cooling-bath was removed and the suspension was stirred for 25 min (a homogenous solution was observed). The organocuprate reagent was cooled back to −78° C. and a solution of allenylazetidinone Ia (128.64 mg, 0.196 mmol in 1.0 mL of THF) was added slowly. The reaction mixture was stirred for 35 min at −78° C. before the reaction was quenched with an aqueous saturated solution of ammonium chloride. After the usual work up and purification (as described in the above Embodiments), the mixture afforded an isomeric mixture of diphenylmethyl 7-phenoxyacetamido-3-Z-propenylceph-3-em-4-carboxylates(IIm) and its Δ-2 isomer (55.3 mg, 52%, 1:1 mixture) and diphenylmethyl 7-phenoxyacetamido-3-methylceph-3-em-4-carboxylate (IIa) (6.1 mg. 6.1%) as a side product. Spectroscopic datas were consistent with the structures.

Embodiment g: In a two necked flask, CuI (152 mg, 0.8 mmol) was placed. One outlet of the flask was connected to nitrogen, while the other outlet was closed using a rubber septum. The flask was evacuated 2 times and purged with nitrogen. A positive pressure of nitrogen was maintained throughout the reaction. Using a syringe, dry tetrahydrofuran (10 mL) followed by Z-1-propenyl tri-n-butylstannane (550 mg, 1.66 mmol) was delivered. The flask was cooled to −78° C. (dry ice-acetone bath), and 1.6M solution of n-butyl lithium in hexanes (1.0 mL, 1.6M solution) was added dropwise. After stirring the reaction mixture for 3 hours at −78° C., a solution of diphenylmethyl 2-[(3R, 4R)-4-(p-toluenesulfonylthio)-3-phenoxyacetamido-2-oxo-azetidin-1-yl]-2,3-butadienoate (Ia) in tetrahydrofuran (0.62 mmol) was added. The cooling bath was removed, and the mixture was stirred for additional 60 minutes before quenching the reaction mixture with a saturated aqueous ammonium chloride solution (10 mL). The aqueous layer was extracted with dichloromethane (10×2 mL), and the organic phase was dried (magnesium sulfate) and concentrated to give a brown oil. Flash chromatography (silica, 40% ethyl acetate in hexanes) of the brown oil afforded 133.9 mg (40%) of the pure title product.

EXAMPLE 33

Diphenylmethyl 7-phenylacetamido-3-Z-propenylceph-3-em-4-carboxylate (IIn)

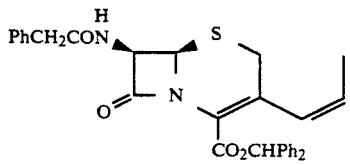

A three necked flask under an atmosphere of argon was charged with copper iodide (67.4 mg, 0.354 mmol) and 6.0 mL of dry THF. The slurry was cooled to −78° C. and while it was being stirred, Z-propenyllithium (0.71 mL, 0.696 mmol, 0.98M solution in diethyl ether) was added slowly. The cooling bath was removed, and after 10 min, the flask was immersed in an ice water bath for 5 min. After recooling the black mixture to −78° C., a THF solution of diphenylmethyl 2-[(3R, 4R)-4-[(benzothiazol-2-yl)dithio]-3-phenylacetamido-2-azetidinon-1-yl]-2,3-butadienoate (Ic) was added dropwise over 3–4 min to the stirred black mixture. After an additional 20 min of stirring, the reaction was quenched by addition of an aqueous saturated ammonium chloride solution (30 mL). After further stirring for 10 min, the content in the flask was transferred into a separatory funnel and diluted with methylene chloride (100 mL). The organic phase was washed with saturated sodium chloride solution (30 mL), dried 15 min over anhydrous magnesium sulfate, filtered and concentrated to afford 68 mg (>100%) of the crude cephem. Preparative chromatography using 35% ethyl acetate in hexanes as the developing solvent gave 34 mg (56%) of the title cephem.

ANALYTICAL DATA $^1$H NMR (CDCl$_3$) δ1.39 (dd, J=1.7 and 7.1 Hz, 3H), 3.23 and 3.40 (ABq, J=18 Hz, 2H), 3.61 and 3.67 (ABq, J=16 Hz, 2H), 4.99 (d, J=4.8 Hz, 1H), 5.54 (dq, J=7.1 and 12 Hz, 1H), 5.82 (dd, J=4.8 and 9.0 Hz, 1H), 6.06 (d, J=12 Hz, 1H), 6.24 (d, J=9.0 Hz, 1H), 6.92 (s, 1H), 7.2–7.45 (m, 15H).

EXAMPLE 34

4-Nitrobenzyl 7-phenoxyacetamido-3-vinyl-3-cephem-4-carboxylate (IIo)

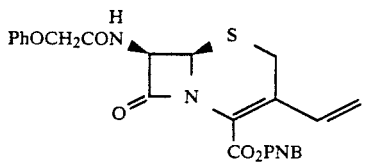

In a two necked flask, copper iodide (96.17 mg, 0.505 mmol) was placed. One outlet of the flask was connected to nitrogen, while the other end was closed using a rubber septum. The flask was evacuated 2 times and purged with nitrogen. A positive pressure of nitrogen was maintained throughout the reaction. Using a syringe, dry tetrahydrofuran (10 mL) followed by vinyltributyl tin (320.26 mg dissolved in 0.3 mL of THF, 1.01 mmol) was delivered. The flask was cooled to −78° C., and a solution of 4-nitrobenzyl 2-[(3R, 4R)-4-(p-toluenesulfonylthio)-3-phenoxyacetamido-2-oxo-azetidin-1-yl]-2,3-butadienoate in tetrahydrofuran (0.388 mmol) was added. The ice bath was removed and the mixture was stirred for additional 2 hours before quenching the reaction mixture with a saturated aqueous ammonium chloride solution (10 mL). The aqueous layer was extracted with dichloromethane (10×3 mL), and the organic phase was dried (magnesium sulfate) and concentrated to give a brown oil. After flash chromatography of the brown oil (silica, 40% ethyl acetate in hexanes), 30.7 mg (16%) of the vinyl cephem, IIo was isolated.

ANALYTICAL DATA $^1$H-NMR (CDCl$_3$, 360 MHz) δ8.24 (d, J=8.0 Hz, 2H), 7.60 (d, J=8.0 Hz, 2H), 7.40–7.0 (m, 6H), 6.92 (d, J =8.0 Hz, 1H), 5.93 (dd, J=4.68 and 9.3 Hz, 1H), 5.54 (d, J=17.8 Hz, 1H), 5.41 (d, J=17.8 Hz, 1H), 5.36 (s, 2H), 5.06 (d, J=4.68 Hz, 1H), 4.56 (s, 2H), 3.72 and 3.54 (ABq, J=18.75 Hz, 2H).

What is claimed is:

1. A process of forming a compound of formula II

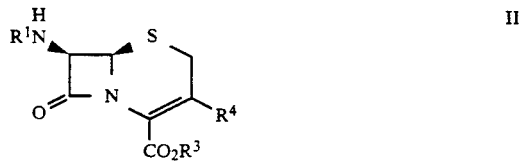

in which R$^1$ is a conventional amino protecting group or an acyl group; R$^2$ is an aromatic heterocyclic or aryl group; R$^3$ is a conventional carboxy protecting group or —CO$_2$R$^3$ taken together forms a physiologically hydrolyzable ester; and R$^4$ is a group selected from the group consisting of C$_{1-6}$ alkyl, C$_{2-6}$ alkenyl, C$_{2-6}$ alkynyl, cyclic C$_{3-6}$ alkyl, and aryl; which comprises the step of reacting an organo-copper reagent with a compound of formula I

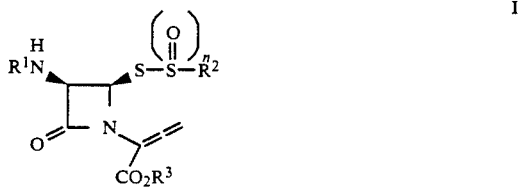

in which R$^1$, R$^2$, and R$^3$ are as defined above and n is 0 or 2.

2. A process as defined in claim 1 in which R$^3$ is a conventional carboxy protecting group and R$^1$ is a conventional amino protecting group or an acyl group represented by a radical R$^a$CO—, in which R$^a$ is hydrogen;

C$_{1-6}$ alkyl, C$_{1-6}$ alkyl substituted by cyano. carboxy, halogen, amino, C$_{1-6}$ alkyloxy, C$_{1-6}$ alkylthio, trifluoromethyl, or trifluoromethylthio;

a phenyl or substituted phenyl group represented by the formula

wherein $R^b$ and $R^c$ independently are hydrogen, halogen, hydroxy, $C_{1-6}$ alkyloxy, $C_{1-6}$ alkyl, $C_{1-6}$ alkylthio, amino, mono- or di($C_{1-6}$ alkyl)amino, $C_{1-6}$ alkanoylamino, $C_{1-6}$ alkylsulfonylamino, carboxy, carbamoyl, hydroxymethyl, aminomethyl, or carboxymethyl;

a group presented by the formula

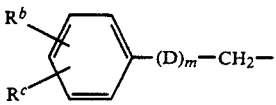

wherein $R^b$ and $R^c$ have the same meanings as defined above, D is oxygen or sulfur, and m is 0 or 1;

a heteroarylmethyl group represented by the formula

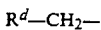

wherein $R^d$ is thienyl, furyl, benzothienyl, benzofuryl, indolyl, triazolyl, tetrazolyl, oxazolyl, thiazolyl, oxadiazolyl, thiadiazolyl, and such heteroaryl groups substituted by amino, hydroxy, halogen, $C_{1-6}$ alkyl, $C_{1-6}$ alkyloxy, $C_{1-6}$ alkysulfonylamino;

a substituted methyl group represented by the formula

wherein $R^e$ is cyclohexa-1,4-dienyl, or a phenyl group or substituted phenyl group

wherein $R^b$ and $R^c$ have the above defined meanings, or $R^e$ is $R^d$ as defined above, and Z is hydroxy, $C_{1-6}$ alkanoyloxy, carboxy, sulfo, or amino;

a keto group or an oximino-substituted group represented by the formulae

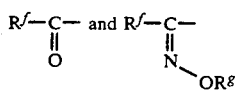

wherein $R^f$ is $R^d$ or $R^e$ as defined above and $R^g$ is hydrogen, $C_{1-6}$ alkyl, cyclic $C_{3-6}$ alkyl or a radical selected from the formulae

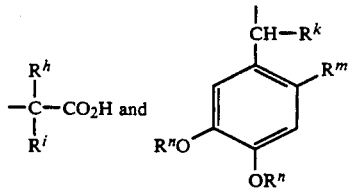

in which $R^h$ and $R^i$ are independently hydrogen, methyl or ethyl, or $R^h$ and $R^i$, taken together with the carbon atom to which they are attached, may be a cycloalkylidene ring containing from 3 to 5 carbon atoms, $R^k$ and $R^m$ are hydrogen or carboxy, with the proviso that both cannot be the same, and $R^n$ is hydrogen or acetyl; or an alkylidene group of the formulae

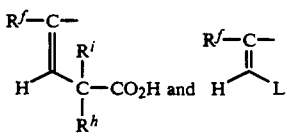

in which L is halogen or $CF_3$, and $R^f$, $R^i$ and $R^h$ are as defined above.

3. A process as defined in claim 2 in which an organo-copper reagent is selected from the group consisting of $R^4$-Cu, $R^4R'CuM$, $R^4LCuM$, $R^4R'R''CuM_2$, $R^4R'LCuM_2$ and $R^4L'L''CuM_2$ in which $R^4$, $R'$ and $R''$ are independently $C_{1-6}$ alkyl, $C_{2-6}$ alkenyl, $C_{3-6}$ cyclic alkyl, aryl, or $C_{2-6}$ alkynyl; L and $L'$ independently represent non-transferable ligands; and M represents a cation.

4. A process as defined in claim 3, in which a non-transferable ligand is selected from the group consisting of $Br^-$, $Cl^-$, $CN^-$, 2-thienyl or $SCN^-$ and a cation is selected from the group consisting of $Li^+$, $^+N(n-Bu)_4$, $^+MgCl$, $^+MgBr$, or $^+MgI$.

5. A process as defined in claim 4, in which $R^1$ is phenoxyacetyl or phenylacetyl; $-S(=O)_nR^2$ is 4-methylphenylsulfonyl or (benzothiazol-2-yl)thio; and $R^3$ is diphenylmethyl or 4-nitrobenzyl.

6. The process as defined in claims 4 or 5, in which the organo-copper reagent is $(CH_3)_2CuMgBr$.

7. The process as defined in claims 4 or 5, in which the organo-copper reagent is $(CH_3)_2CuLi$.

8. The process as defined in claims 4 or 5, in which the organo-copper reagent is $(CH_2CH_3)_2CuMgBr$.

9. The process as defined in claims 4 or 5, in which the organo-copper reagent is $(isopropyl)_2CuMgBr$.

10. The process as defined in claims 4 or 5, in which the organo-copper reagent is $(n-butyl)_2CuMgBr$.

11. The process as defined in claims 4 or 5, in which the organo-copper reagent is $(t-butyl)_2CuMgBr$.

12. The process as defined in claims 4 or 5, in which the organo-copper reagent is $(hexyl)_2CuMgBr$.

13. The process as defined in claims 4 or 5, in which the organo-copper reagent is $(Ph)_2CuMgBr$.

14. The process as defined in claims 4 or 5, in which the organo-copper reagent is $(cyclohexyl)_2CuMgBr$.

15. The process as defined in claims 4 or 5, in which the organo-copper reagent is $(cyclopentyl)_2CuMgBr$.

16. The process as defined in claims 4 or 5, in which the organo-copper reagent is $(vinyl)_2CuMgBr$.

17. The process as defined in claims 4 or 5, in which the organo-copper reagent is $(CH=CHCH_2)_2CuMgBr$.

18. The process as defined in claims 4 or 5, in which the organo-copper reagent is $(Z-CH_3CH=CH)_2CuMgBr$.

19. The process as defined in claims 4 or 5, in which the organo-copper reagent is $(Z-CH_3CH=CH)_2CuLi$.

20. The process as defined in claims 4 or 5, in which the organo-copper reagent is $(vinyl)_2CuLi$.

21. The process as defined in claims 4 or 5, in which the organo-copper reagent is $(Z-CH_3CH=CH)(CH_3)CuLi$.

* * * * *